United States Patent
Sasou et al.

(10) Patent No.: US 9,933,679 B2
(45) Date of Patent: Apr. 3, 2018

(54) BIREFRINGENCE IMPROVING AGENT, FERROELECTRIC LIQUID CRYSTAL COMPOSITION AND LIQUID CRYSTAL DISPLAY DEVICE USING THE AGENT, AND COMPOUND

(71) Applicant: LC VISION, LLC, Boulder, CO (US)

(72) Inventors: Naoki Sasou, Tokyo (JP); Sumio Maruyama, Tokyo (JP); Tetsunori Matsushita, Tokyo (JP); Michael Wand, Boulder, CO (US)

(73) Assignee: LC Vision, LLC, Boulder, CO (US)

( * ) Notice: Subject to any disclaimer, the term of this patent is extended or adjusted under 35 U.S.C. 154(b) by 0 days.

(21) Appl. No.: 14/906,247

(22) PCT Filed: Jul. 17, 2013

(86) PCT No.: PCT/US2013/050783
§ 371 (c)(1),
(2) Date: Jan. 19, 2016

(87) PCT Pub. No.: WO2015/009290
PCT Pub. Date: Jan. 22, 2015

(65) Prior Publication Data
US 2016/0161817 A1    Jun. 9, 2016

(51) Int. Cl.
*G02F 1/1333*    (2006.01)
*G02F 1/141*    (2006.01)
*C09K 19/02*    (2006.01)
*C09K 19/12*    (2006.01)
*C09K 19/30*    (2006.01)
*C07C 69/753*    (2006.01)
*C09K 19/34*    (2006.01)
*G02F 1/1337*    (2006.01)
*C09K 19/04*    (2006.01)

(52) U.S. Cl.
CPC .......... *G02F 1/141* (2013.01); *C07C 69/753* (2013.01); *C09K 19/0225* (2013.01); *C09K 19/126* (2013.01); *C09K 19/3068* (2013.01); *C09K 19/3458* (2013.01); *G02F 1/1337* (2013.01); *C07C 2101/14* (2013.01); *C09K 2019/0437* (2013.01); *C09K 2019/125* (2013.01)

(58) Field of Classification Search
CPC .............. C09K 19/0225; C09K 19/126; C09K 19/3068; C09K 19/3458; C09K 2019/0437; C09K 2019/125; G02F 1/1333; G02F 1/141; G02F 1/1337; C07C 69/753; C07C 2101/14
USPC .............. 252/299.01, 299.6, 299.63; 428/1.1
See application file for complete search history.

(56) References Cited

U.S. PATENT DOCUMENTS

| 5,151,803 A * | 9/1992 | Wakita ................... G02F 1/141 345/97 |
| 5,190,692 A | 3/1993 | Coates et al. |
| 7,057,700 B2 | 6/2006 | Sugimoto et al. |
| 8,580,142 B2 | 11/2013 | Shimada et al. |
| 2003/0098945 A1 | 5/2003 | Sugimoto et al. |
| 2010/0301270 A1 | 12/2010 | Kim et al. |
| 2010/0328600 A1 | 12/2010 | Shimada et al. |

FOREIGN PATENT DOCUMENTS

| JP | H02279649 | 11/1990 |
| JP | 2001-034197 | 2/2001 |
| JP | 3225084 B2 | 11/2001 |

OTHER PUBLICATIONS

International Search Report for PCT/US2013/050783 dated Jan. 3, 2014.

\* cited by examiner

*Primary Examiner* — Geraldina Visconti
(74) *Attorney, Agent, or Firm* — Lathrop Gage LLP

(57) ABSTRACT

A main object of the present invention is to provide a birefringence improving agent that can realize a satisfactory white display even in a liquid crystal display device in which a ferroelectric liquid crystal composition is used and which can reduce the birefringence and has a large cell gap; a ferroelectric liquid crystal composition and a liquid crystal display device that use the birefringence improving agent; and a compound that can be used in a ferroelectric liquid crystal composition.

16 Claims, 2 Drawing Sheets

BIREFRINGENCE IMPROVING AGENT, FERROELECTRIC LIQUID CRYSTAL COMPOSITION AND LIQUID CRYSTAL DISPLAY DEVICE USING THE AGENT, AND COMPOUND

CROSS REFERENCE TO RELATED APPLICATIONS

The present application is a U.S. National Stage application under 35 U.S.C. 371 of International Application Number PCT/US2013/050783, filed in English on Jul. 17, 2013, the entirety of which is incorporated herein by reference.

TECHNICAL FIELD

The present invention relates to a ferroelectric liquid crystal composition and a liquid crystal display device, both of which have low birefringence, and a compound which can be used in a ferroelectric liquid crystal composition.

BACKGROUND ART

With the features of being thin and capable of consuming less electric power, liquid crystal display devices have a wide variety of applications ranging from large-sized displays to portable information terminals, and thus development of the liquid crystal display devices is inactive progress. In regard to liquid crystal display devices developed thus far, multiplex drive for the TN mode and STN, active matrix drive using a thin film transistor (TFT) for TN, and the like have been developed and put to practical use. However, since these drive modes use nematic liquid crystals, the response speeds of the liquid crystal materials are as slow as several milliseconds (ms) to several ten milliseconds (ms), and it cannot be said that the liquid crystal materials are sufficiently capable of coping with moving video image displays.

Ferroelectric liquid crystals are liquid crystals which have response speeds that are very short in the order of microseconds (μs), and are appropriate for high speed devices. Since ferroelectric liquid crystals have superiority such as wide viewing angles, it is expected that high performance liquid crystal display devices can be provided.

Since ferroelectric liquid crystals have high birefringence, in a liquid crystal display device which uses a ferroelectric liquid crystal, in order to suppress the occurrence of color shift and thereby obtain a satisfactory white display, it is necessary to make the cell gap very narrow to less than 2 μm. However, with a narrow cell gap, there is a problem that due to the occurrence of thickness unevenness, and to the occurrence of color unevenness or display unevenness caused by thickness unevenness, the yield in production is decreased.

Thus, a ferroelectric liquid crystal which can realize satisfactory white display even in a liquid crystal display device having a large cell gap is desired.

For the purpose of providing a liquid crystal display device which enables a black-and-white display with high visibility by preventing coloration caused by a birefringence effect, for example, Patent Document 1 suggests that a substrate is made to exhibit birefringence, and also, the principal optical axis of the substrate is disposed to be slanting by 30° from the normal line of the smectic layer of the ferroelectric liquid crystal, to thereby adjust the difference in retardation of the substrate and the liquid crystal layer to a predetermined range.

Furthermore, although not related to ferroelectric liquid crystals, in regard to nematic liquid crystals, it is known to add a liquid crystal material in order to improve display characteristics. For example, Patent Document 2 suggests adding a liquid crystal material having a desired birefringence or a liquid crystal material having a relatively high birefringence.

Furthermore, in Patent Document 3, although not related to ferroelectric liquid crystals, in regard to nematic liquid crystals, a tetracyclic ester compound and an ether compound, both of which have a predetermined structure having a benzene ring and three cyclohexane rings in total introduced into the main chain, are disclosed for the purpose of providing a liquid crystalline compound which is suitable for super-twist displays.

CITATION LIST

Patent Literature

Figure 1:
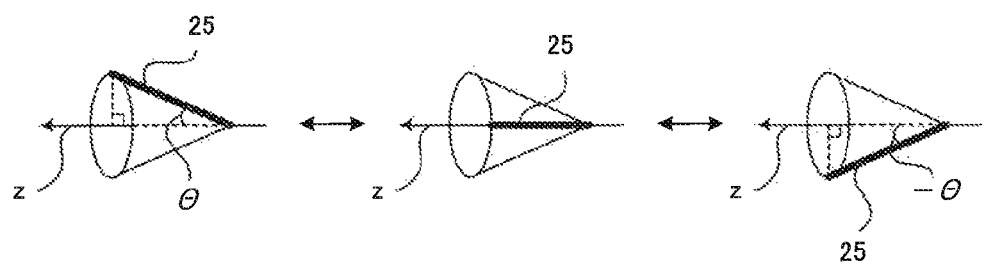
FIG. 1 is a schematic diagram illustrating an example of the alignment state of liquid crystal molecules in the present invention.

Patent Literature 1: Japanese Patent No. 3225084
Patent Literature 2: Japanese Patent Application Publication Laid-Open (JP-A) No. 2001-034197
Patent Literature 3: JP-A No. H02-279649

SUMMARY OF INVENTION

Technical Problem

In Patent Literature 1, birefringence is improved by adjusting the difference in retardation between the substrate and the liquid crystal layer of a liquid crystal display device to a predetermined range, and the invention is not intended to reduce the birefringence of a ferroelectric liquid crystal itself.

Furthermore, in Patent Literature 2, a liquid crystal material which exhibits high birefringence is used.

Furthermore, Patent Literature 3 has no description regarding the reduction of birefringence of a ferroelectric liquid crystal composition.

The present invention was achieved in view of the problems described above, and it is a principal object of the present invention to provide a birefringence improving agent that can reduce birefringence in a liquid crystal display device in which a ferroelectric liquid crystal composition is used, and is capable of realizing a satisfactory white display even in a liquid crystal display device having a large cell gap; a ferroelectric liquid crystal composition and a liquid crystal display device that use the agent; and a compound that can be used in a ferroelectric liquid crystal composition.

Solution to Problem

The inventors of the present invention repeatedly conducted investigations on the birefringence of liquid crystal display devices in which ferroelectric liquid crystals are used, and as a result, the inventors found that when a compound having a particular structure is used in a ferroelectric liquid crystal composition, birefringence can be reduced, and when the ferroelectric liquid crystal composition is used in a liquid crystal display device, the occurrence of color shift is suppressed, and a satisfactory white display is obtained. Thus, the inventors eventually completed the present invention based on such findings.

That is, the present invention provides a birefringence improving agent having a structure represented by the following general formula (1):

[Chemical Formula 1]

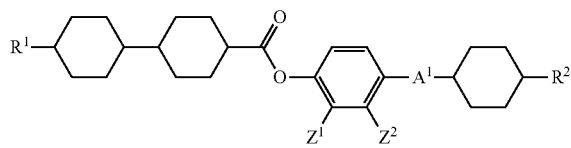

(1)

wherein in the formula (1), $R^1$ and $R^2$ each represent a linear or branched alkyl group having 3 to 9 carbon atoms, provided that at least one of $R^1$ and $R^2$ has 5 or more carbon atoms;

$A^1$ represents —$CH_2$—$CH_2$—, —O—$CH_2$— or —$CH_2$—O—; and $Z^1$ and $Z^2$ each independently represent a fluorine atom or a hydrogen atom.

The birefringence improving agent of the present invention, which has a structure represented by the above formula (1), can reduce birefringence when added to a ferroelectric liquid crystal composition. In a liquid crystal display device in which the ferroelectric liquid crystal composition is used, even if the cell gap is relatively large, the occurrence of color shift is suppressed, and a satisfactory white display can be realized.

Furthermore, the present invention provides a ferroelectric liquid crystal composition containing a birefringence improving agent represented by the formula (1).

The ferroelectric liquid crystal composition of the present invention, which contains a birefringence improving agent represented by the formula (1), can reduce birefringence.

Furthermore, the present invention provides a liquid crystal display device comprising: a first alignment treatment substrate comprising a first base material, a first electrode layer formed on the first base material, and a first alignment layer formed on the first electrode layer; a second alignment treatment substrate comprising a second base material, a second electrode layer formed on the second base material, and a second alignment layer formed on the second electrode layer; and a liquid crystal layer that is formed between the first alignment layer and the second alignment layer and contains a ferroelectric liquid crystal composition, wherein the ferroelectric liquid crystal composition containing a birefringence improving agent represented by the formula (1)

Since the liquid crystal display device of the present invention uses a ferroelectric liquid crystal composition containing a birefringence improving agent represented by the formula (1), birefringence of the ferroelectric liquid crystal composition can be reduced, and a satisfactory white display can be realized.

Furthermore, the present invention provides a compound having a structure represented by the following general formula (2):

[Chemical Formula 2]

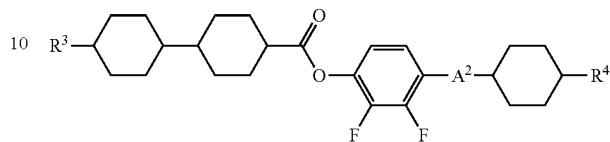

(2)

wherein in the formula (2), $R^3$ and $R^4$ each represent a linear or branched alkyl group having 3 to 9 carbon atoms, provided that at least one of $R^3$ and $R^4$ has 5 or more carbon atoms; and $A^2$ represents —O—$CH_2$— or —$CH_2$—O—.

The compound of the present invention, which has a structure represented by the above formula (2), can reduce birefringence when the compound is added to a ferroelectric liquid crystal composition. In a liquid crystal display device in which the ferroelectric liquid crystal composition is used, even if the cell gap is relatively large, the occurrence of color shift is suppressed, and a satisfactory white display can be realized.

Advantageous Effects of Invention

The birefringence improving agent represented by the formula (1) of the present invention can reduce birefringence when used in a ferroelectric liquid crystal composition. Furthermore, when the ferroelectric liquid crystal composition is used in a liquid crystal display device, there is provided an effect that the occurrence of color shift is suppressed and a satisfactory white display can be realized.

DESCRIPTION OF EMBODIMENTS

Hereinafter, the birefringence improving agent, ferroelectric liquid crystal composition, liquid crystal display device, and compound of the present invention will be described in detail.

A. Birefringence Improving Agent

The birefringence improving agent of the present invention has a structure represented by the following general formula (1):

[Chemical Formula 3]

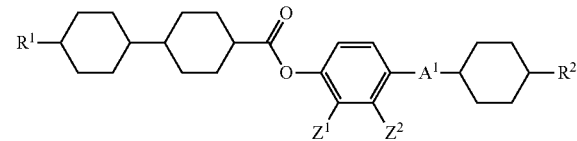

(1)

wherein in the formula (1), $R^1$ and $R^2$ each represent a linear or branched alkyl group having 3 to 9 carbon atoms, provided that at least one of $R^1$ and $R^2$ has 5 or more carbon atoms;

$A^1$ represents —$CH_2$—$CH_2$—, —O—$CH_2$— or —$CH_2$—O—; and $Z^1$ and $Z^2$ each independently represent a fluorine atom or a hydrogen atom.

That is, the birefringence improving agent of the present invention is represented by any one of the following general formulae (1-1) to (1-3):

[Chemical Formula 4]

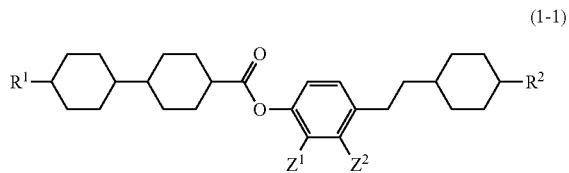

(1-1)

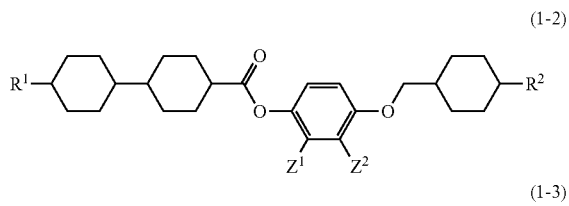

(1-2)

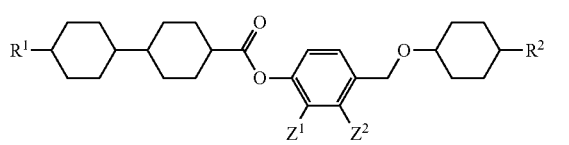

(1-3)

wherein in the formulae (1-1) to (1-3), $R^1$, $R^2$, $Z^L$ and $Z^2$ have the same meanings as those defined in the above formula (1), respectively.

In general, a liquid crystalline compound has a structure composed of a core section, terminal chain sections, and spacer sections that links the core section and the terminal chain sections, and has a rod-like shape. It is general that a liquid crystalline compound which constitutes a ferroelectric liquid crystal composition also has such a structure and such a shape. Particularly, a liquid crystalline compound which constitutes a ferroelectric liquid crystal composition has a plural number of aromatic rings such as a benzene ring and a pyrimidine ring at the core section, and tends to have a linear shape, so that anisotropy of the refractive index, that is, birefringence increases.

Furthermore, it is known that as there are more conjugates based on unsaturated bonds, birefringence increases.

On the other hand, since the birefringence improving agent represented by the formula (1) has not a rod shape but a bent shape, anisotropy of the refractive index decreases. Furthermore, since the birefringence improving agent represented by the formula (1) only has one benzene ring at the core section and does not have plural aromatic rings, there are fewer conjugates based on unsaturated bonds. Accordingly, it is speculated that birefringence is reduced thereby.

Therefore, birefringence can be reduced by adding a birefringence improving agent represented by the formula (1) to a ferroelectric liquid crystal composition. Therefore, when the ferroelectric liquid crystal composition is used in a liquid crystal display device having a relatively large cell gap, the occurrence of color shift is suppressed, and thereby a satisfactory white display can be obtained.

1. Birefringence Improving Agents Represented by Formulae (1-1) to (1-3)

In the formulae (1-1) to (1-3), $R^1$ represents a linear or branched alkyl group.

It is acceptable if the number of carbon atoms of $R^1$ is 3 to 9, but above all, the number of carbon atoms is preferably 5 to 7, and particularly preferably 5. If the number of carbon atoms is larger than the range described above, when the birefringence improving agent is added to a ferroelectric liquid crystal composition, there is a risk that the ferroelectric liquid crystal composition may become likely to exhibit a liquid crystalline phase which is close to a crystalline phase such as the smectic B phase. When a liquid crystalline phase which is close to a crystalline phase such as the smectic B phase is exhibited, the regularity of the molecular arrangement increases excessively, and impact resistance may decrease, or the phase sequences may become complicated, so that it may be difficult for liquid crystal molecules to align themselves. Furthermore, the tilt angle of the liquid crystal molecules may become extremely small, and there is a risk that the drive performance may deteriorate, such as that sufficient brightness may not be obtained. On the other hand, if the number of carbon atoms is smaller than the range described above, there is a risk that the temperature range of the chiral smectic C phase of the ferroelectric liquid crystal composition may be narrowed, or there is a risk that the chiral smetic C phase may not be exhibited. If the temperature range of the chiral smectic C phase is narrowed, the tilt angle of the liquid crystal molecules may become extremely small, or the alignment of the liquid crystal molecules may be adversely affected. When the number of carbon atoms is within the range described above, the tilt angle of the liquid crystal molecules becoming extremely small can be suppressed, and satisfactory drive performance can be obtained.

Incidentally, the number of carbon atoms of at least one of $R^1$ and $R^2$ that will be described below is 5 or greater. The reason for this is the same as that in the case where the number of carbon atoms of $R^1$ described above is in a predetermined range.

In the formulae (1-1) to (1-3), $R^2$ represents a linear or branched alkyl group.

It is acceptable if the number of carbon atoms of $R^2$ is 3 to 9, and above all, the number of carbon atoms is preferably 5 to 7, and particularly preferably 5. Since the reason why the number of carbon atoms of $R^2$ is preferably in the range described above, is the same as the reason for the number of carbon atoms of $R^1$ described above, further description will not be repeated herein.

In the formulae (1-1) to (1-3), $Z^1$ and $Z^2$ each independently represent a fluorine atom or a hydrogen atom. Among others, it is preferable that at least one of $Z^1$ and $Z^2$ be a fluorine atom. When at least one of $Z^1$ and $Z^2$ is a fluorine atom, the tilt angle of the liquid crystal molecules can be made large, and therefore, the transmittance of the liquid crystal display device can be increased. Furthermore, since the range of the phase transition temperature of the chiral smectic C phase is broadened, in the case where a ferroelectric liquid crystal composition having a compound represented by any one of the formulae (1-1) to (1-3) is used in a liquid crystal display device, the liquid crystal display device can be driven in a stable manner at low temperatures and at high temperature.

Specific examples of the birefringence improving agents represented by the formulae (1-1) to (1-3) include birefringence improving agents represented by the following formulae:

[Chemical Formula 5]

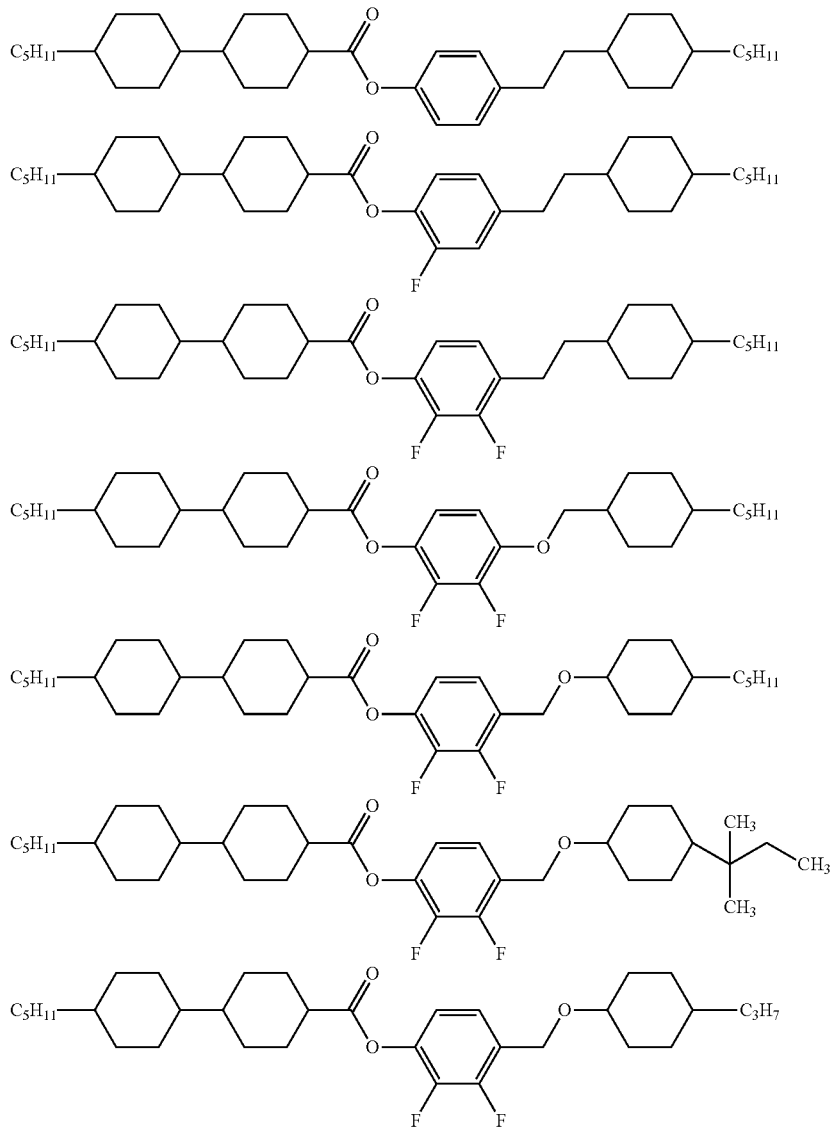

2. Synthesis method

The birefringence improving agents of the present invention can be synthesized from an arbitrary raw material compound, using a generally known organic synthesis method. Hereinafter, the methods for synthesizing birefringence improving agents represented by the formulae (1-1) to (1-3) will be described.

(1) Birefringence Improving Agent Represented by Formula (1-1)

The birefringence improving agent represented by the formula (1-1) can be synthesized by, for example, the method described in JP-A No. H02-279649.

(2) Birefringence Improving Agent Represented by Formula (1-2)

As an example of the method for synthesizing a birefringence improving agent represented by the formula (1-2), a method for synthesizing a birefringence improving agent represented by the following formula (1-4) will be described in divided sections of from a first process to a fifth process.

[Chemical Formula 6]

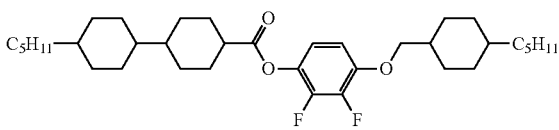

(1-4)

(a) First process

First, in a nitrogen atmosphere, LiAlH$_4$ is added to ice-cooled anhydrous THF, and the mixture is stirred. A 4-trans-pentylcyclohexanecarboxylic acid solution dissolved in anhydrous THF is added dropwise thereto, and subsequently, the mixture is returned to room temperature and stirred. Next, water and an aqueous NaOH solution are added to this solution, the mixture is stirred, and insoluble materials are removed by performing Celite filtration. Subsequently, the mixture is subjected to extraction, washing with water, drying, concentration, and drying under reduced pressure, and thereby colorless, oily 4-trans-n-pentylcyclohexanemethanol can be obtained.

(b) Second process

In a nitrogen atmosphere, a solution in which 2,3-difluorophenol and the compound obtained in the above-described "(a) First process" are dissolved in anhydrous THF is prepared, triphenylphosphine is added thereto, and the mixture is ice-cooled. Diisopropyl azodicarboxylate is added dropwise thereto, and the mixture is stirred. Thereafter, the mixture is returned to room temperature and stirred, and the mixture is subjected to extraction, washing with water, drying, and concentration. Thereby, a yellow oily substance can be obtained. Subsequently, N-hexane is added to the oily substance, and a white solid that has precipitated out at this time is removed by filtration and concentrated. Thereafter, the white solid is subjected to purification, and thereby 4-trans-n-pentyl-1-(2,3-difluorophenoxymethyl)cyclohexane as a white solid can be obtained.

(c) Third process

In an Ar atmosphere, a solution in which the compound obtained in the "(b) Second process" is dissolved in anhydrous THF is stirred at or below −40° C., a butyllithium hexane solution is added dropwise thereto, and the mixture is stirred. Next, trimethoxyborane is added dropwise to the solution thus obtained, and the mixture is stirred. Next, this solution is returned to room temperature, and a dilute aqueous hydrochloric acid solution is added thereto to acidify the solution. This solution is stirred, and is subjected to extraction, drying, and concentration under reduced pressure. Thereafter, N-hexane is added to the residue thus obtained, the mixture is ice-cooled, and crystals precipitated therefrom are collected by filtration. Thereby, 4-(4-trans-n-pentylcyclohexylmethyloxy)-2,3-difluorophenylboronic acid as a white powder can be obtained.

(d) Fourth process

Acetic acid is added to the compound obtained in the "(c) Third process", and subsequently, an aqueous hydrogen peroxide solution is added thereto at room temperature. Next, this solution is stirred, water is added thereto, and crystals precipitated therefrom are collected by filtration. Thereby, 4-(4-trans-n-pentylcyclohexylmethyloxy)-2,3-difluorophenol as a pale yellow powder can be obtained.

(e) Fifth process

In a nitrogen atmosphere, triethylamine is added to a solution in which the compound obtained in the "(d) Fourth process" is dissolved in anhydrous methylene chloride, and the mixture is ice-cooled. To this solution, a solution prepared by dissolving 4-trans-4-(trans-4-n-pentylcyclohexyl)cyclohexylcarbonyl chloride in methylene chloride is added dropwise, and the mixture is stirred. Next, this solution is returned to room temperature and stirred, and the solution is subjected to extraction, washing with water, drying, and concentration under reduced pressure. Thereafter, methanol is added to the residue thus obtained, the mixture is stirred at room temperature, and crystals precipitated therefrom are collected by filtration. Thereby, a birefringence improving agent represented by the formula (1-4) as a white solid, which is the final product, can be obtained.

(3) Birefringence improving agent represented by formula (1-3)

As an example of the method for synthesizing a birefringence improving agent represented by the formula (1-3), a method for synthesizing a birefringence improving agent represented by the following formula (1-5) will be described in divided sections of from a first process to a seventh process.

[Chemical Formula 7]

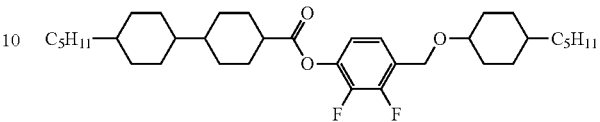

(1-5)

(a) First process

First, 2,3-difluorophenol and potassium carbonate are added to DMF in the presence of benzyl bromide, and the mixture is heated in an Ar atmosphere and then stirred. Next, the mixture is subjected to extraction, washing with water, drying, concentration, and drying under reduced pressure, and thereby oily 2,3-difluorophenyl benzyl ether can be obtained.

(b) Second process

In an Ar atmosphere, the compound obtained in the "(a) First process" is added to THF, and the mixture is stirred at or below −40° C. A butyllithium hexane solution is added dropwise thereto. Subsequently, this solution is stirred, and then dry ice is added thereto. The mixture is stirred overnight. Thereafter, the mixture is subjected to extraction, drying, concentration, and recrystallization, and thereby 4-benzyloxy-2,3-difluorobenzoic acid as a white solid can be obtained.

(c) Third process

In an Ar atmosphere, the compound obtained in the "(b) Second process" is added to THF and trimethoxyborane, and the mixture is stirred under ice cooling. Subsequently, to this solution, a THF solution of a borane-dimethyl sulfide complex is added dropwise, and the mixture is stirred overnight at room temperature. Thereafter, this solution is poured into ice water, and a precipitate thus obtained is collected by filtration and dried under reduced pressure. Thereby, 4-benzyloxy-2,3-difluorobenzyl alcohol as a white solid can be obtained.

(d) Fourth process

In an Ar atmosphere, the compound obtained in the "(c) Third process" is added to dichloromethane, and the mixture is stirred at room temperature. To this solution, a dichloromethane solution of phosphorus tribromide is added dropwise, the mixture is stirred overnight at room temperature, and ice water is poured thereinto to perform separation. Thereafter, the resultant is subjected to washing with water, drying, concentration, and drying under reduced pressure, and thereby, 4-benzyloxy-2,3-difluorobenzyl bromide as a white solid can be obtained.

(e) Fifth process

In an Ar atmosphere, the compound obtained in the "(d) Fourth process", trans-pentylcyclohexanol and sodium hydride are added to THF and DMF, and the mixture is heated and then stirred overnight. Next, the mixture is subjected to extraction, washing with water, drying, concentration, and purification, and thereby 2,3-difluoro-4-(trans-pentylcyclohexyl)oxymethylphenyl benzyl ether as a white solid can be obtained.

(f) Sixth process

In a hydrogen atmosphere, the compound obtained in the "(e) Fifth process", palladium carbon, and concentrated hydrochloric acid are added to THF and ethanol, and the mixture is heated and then stirred overnight. Thereafter, the mixture is subjected to filtration, concentration, and purification, and thereby 2,3-difluoro-4-(trans-pentylcyclohexyl) oxymethylphenol as a white solid can be obtained.

(g) Seventh process

In an Ar atmosphere, the compound obtained in the "(f) Sixth process", trans, trans-4-(4'-pentylcyclohexyl)cyclohexylcarbonyl chloride, and triethylamine are added to dichloromethane, and the mixture is stirred overnight at room temperature. Next, the mixture is subjected to extraction, washing with water, drying, concentration, purification, and recrystallization, and thereby a birefringence improving agent represented by the formula (1-5) as a white solid can be obtained.

3. Use

The birefringence improving agent represented by the formula (1) is such that as the birefringence improving agent is contained in the ferroelectric liquid crystal composition described above, when the ferroelectric liquid crystal composition is used in a liquid crystal display device, the occurrence of color shift is suppressed, and a satisfactory white display can be obtained.

Here, in the case where a ferroelectric liquid crystal composition containing a birefringence improving agent represented by the formula (1) is used in a liquid crystal display device, regarding the birefringence improving agent represented by the formula (1), one kind may be used singly, or two or more kinds may be used in mixture.

B. Ferroelectric Liquid Crystal Composition

The ferroelectric liquid crystal composition of the present invention comprises a birefringence improving agent represented by the formula (1).

According to the ferroelectric liquid crystal composition of the present invention, as the composition contains a birefringence improving agent represented by the formula (1), birefringence can be reduced while the drive performance is maintained.

Hereinafter, various components for the ferroelectric liquid crystal composition of the present invention will be described.

1. Birefringence Improving Agent Represented by Formula (1)

The birefringence improving agent represented by the formula (1) will be described.

The birefringence improving agent represented by the formula (1) that is used in the ferroelectric liquid crystal composition of the present invention may be of only one kind, or may include two or more kinds.

The content of the birefringence improving agent represented by the formula (1) in the ferroelectric liquid crystal composition of the present invention is not particularly limited as long as the birefringence improving agent can reduce birefringence. However, the content is preferably in the range of 5% by mass to 60% by mass in the ferroelectric liquid crystal composition of the present invention, and above all, the content is preferably in the range of 10% by mass to 50% by mass, and particularly preferably in the range of 10% by mass to 30% by mass. If the content of the birefringence improving agent represented by the formula (1) is small, the effect of reducing birefringence may not be sufficiently obtained. On the other hand, if the content of the birefringence improving agent represented by the formula (1) is large, viscosity increases, and the response speed may decrease, or the driving voltage may increase. Furthermore, if the content of the birefringence improving agent is large, the temperature range of the chiral smectic C phase may shift toward the higher temperature side, and thereby the phase transition temperature on the lower temperature side may approach room temperature. Alternatively, a single component in the ferroelectric liquid crystal composition may increase, and thereby crystallization may easily occur.

Incidentally, since the details of the birefringence improving agent represented by the formula (1) are the same as described in the section "A. Birefringence improving agent represented by formula (1)", further explanation will not be repeated here.

2. Chiral compound

The ferroelectric liquid crystal composition of the present invention usually contains a chiral compound.

Regarding the chiral compound that is used in the present invention, compounds that are generally used as chiral compounds for ferroelectric liquid crystal compositions can be used. Incidentally, it is neither necessary for the chiral compound to have smectic properties, nor to exhibit liquid crystallinity.

Among others, the chiral compound is preferably such that two or more benzene rings are directly linked together, and more preferably such that three or more benzene rings are directly linked together. Since a benzene ring adopts a planar structure, a chiral compound in which two or more benzene rings are directly linked has a tendency that the benzene ring planes are aligned to be laminated. For this reason, the refractive index in a direction parallel to the benzene ring plane and the refractive index in a direction perpendicular to the benzene ring plane differ greatly from each other, and birefringence is easily increased. On the other hand, with regard to the present invention, since birefringence can be reduced, it is effective in the case where such a chiral compound is used.

Furthermore, the chiral compound in which three or more benzene rings are directly linked is preferably at least one of a chiral compound A represented by the following general formula (3) and a chiral compound B represented by the following general formula (4). When such a chiral compound is contained, in the case of using the ferroelectric liquid crystal composition of the present invention in a liquid crystal display device, impact resistance can be enhanced. Since ferroelectric liquid crystals have higher orderliness of molecules compared with nematic liquid crystals, if the regularity of molecular orientation is disordered by impact, the molecular orientation does not easily return to the original state, that is, the liquid crystals are very vulnerable to external impact. Therefore, it, is preferable that impact resistance be satisfactory.

In the present invention, as described above, when a ferroelectric liquid crystal composition contains such a chiral compound that improves impact resistance, birefringence can be reduced while impact resistance is maintained.

Incidentally, since the chiral compound A and the chiral compound B have three or more benzene rings at the core section, birefringence is especially likely to increase. However, as explained in the above, since at least one compound of the birefringence improving agents represented by the formula (1) is contained in the present invention, the birefringence of the ferroelectric liquid crystal composition can be reduced.

Hereinafter, the chiral compound according to the present invention will be described separately in terms of the chiral compound A and the chiral compound B.

(1) Chiral compound A

The chiral compound A that is used in the present invention is a compound represented by the following general formula (3):

[Chemical Formula 8]

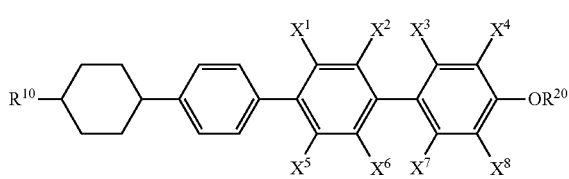
(3)

wherein in the formula (3), $R^{10}$ is a non-chiral group and represents a saturated or unsaturated alkyl group or alkoxyalkyl group which may be substituted with a halogen atom.

The number of carbon atoms is desirably 4 to 18, but above all, the number of carbon atoms is preferably 6 to 1.8, and more preferably 6 to 12. It is because if the number of carbon atoms is larger than the range described above, synthesis of the chiral compound A becomes difficult, and the cost increases. On the other hand, it is because if the number of carbon atoms is smaller than the range described above, the ferroelectric liquid crystal composition may not exhibit the smectic phase. The alkyl group or alkoxyalkyl group may be substituted with a halogen atom, or may not be substituted with a halogen atom.

The alkyl group or alkoxyalkyl group is linear or branched.

$R^{20}$ is a chiral group and represents a group represented by the following general formula (5):

[Chemical Formula 9]

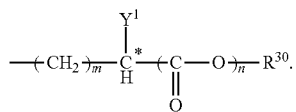
(5)

In the formula (5), $R^{30}$ represents a saturated or unsaturated linear, branched or cyclic alkyl group or alkoxyalkyl group having 1 to 10 carbon atoms, which may be substituted with a halogen atom.

In the formula (5), $Y^1$ represents —$CH_3$ or a fluorine atom. $Y^1$ may be —$CH_3$ or may be a fluorine atom, but above all, $Y^1$ is preferably —$CH_3$. It is because, as described above, synthesis of the chiral compound A is feasible, the chiral compound A can be produced in a stable manner, and a ferroelectric liquid crystal composition can be obtained inexpensively.

In the formula (5), "m" represents 0 or 1, and "n" represents 0 or 1.

Furthermore, in the formula (5), symbol * represents the chiral center. When m=0, the carbon atom at the 1-position serves as the chiral center, and when m=1, the carbon atom at the 2-position serves as the chiral center.

Also, since $R^{20}$ in the formula (5) is a chiral group, in the formula (5), when $Y^1$ is —$CH_3$ and n=0, $R^{30}$ is not —$CH_3$.

In the formula (3), $X^1$ to $X^8$ each independently represent —$CH_3$, —$CF_3$, a halogen atom, or a hydrogen atom. However, one or more of $X^1$ to $X^8$ each independently represent —$CH_3$, —$CF_3$, or a halogen atom.

When all of $X^1$ to $X^8$ are hydrogen atoms, since the solubility of the chiral compound A decreases, synthesis and purification of the chiral compound A become difficult, and there is a risk that the cost may increase. On the contrary, when one or more of $X^1$ to $X^8$ represent —$CH_3$, —$CF_3$ or a halogen atom as in the case of the present invention, the solubility of the chiral compound A in a solvent increases, and synthesis and purification in large quantities are enabled. Furthermore, it is speculated that since a strain occurs in the steric structure of the chiral compound A, and this strain loosens the molecular arrangement that is excessively regular, high impact resistance can be obtained.

Above all, it is preferable that any one or more of $X^1$ to $X^3$ and $X^5$ to $X^7$ be each independently —$CH_3$, —$CF_3$ or a halogen atom. It is because when the compound has substituents at the positions of $X^1$ to $X^3$ and $X^5$ to $X^7$, the chiral compound has superior solubility than in the case of the positions of $X^4$ and $X^8$. This is speculated to be because the case of the positions of $X^4$ and $X^8$ involves less strain caused by substituents as compared with the case of other positions.

One benzene ring may have 1 to 4 substituents, but among others, it is preferable that a benzene ring have one or two substituents. When there is one substituent, the substituent is preferably —$CH_3$, a fluorine atom or a chlorine atom, and above all, the substituent is preferably —$CH_3$ or a fluorine atom. On the other hand, when there are two substituents, it is preferable that both substituents be fluorine atoms in this case, regarding the positions of the two substituents, for example, it is preferable that adjoining carbon atoms of a benzene ring be each substituted by a fluorine atom, as in the case where $X^1$ and $X^2$, or $X^3$ and $X^4$ are fluorine atoms. When adjoining carbon atoms of a benzene ring are respectively substituted by two fluorine atoms, and the benzene ring is symmetrically substituted, the chiral smectic C phase is stabilized, and the tilt angle of the liquid crystal molecules can be made large. Therefore, the transmittance of the liquid crystal display device can be increased. Furthermore, since two substituents are bonded to carbon atoms that are located closer to each other, the regularity of the molecular arrangement can be loosened, and crystallization can be suppressed.

Furthermore, it is preferable that the chiral compound represented by the formula (3) have one to two substituents in total.

In regard to the chiral compound represented by the formula (3), it is preferable that one benzene ring between the benzene rings to which $X^1$ to $X^8$ are bonded, have substituents, and above all, it is preferable that the benzene ring to which $X^1$, $X^2$, $X^5$ and $X^6$ are bonded have substituents. It is because if the benzene ring that is located in the middle among the three benzene rings that are directly linked, has a substituent, it is difficult for the ferroelectric liquid crystal composition to be crystallized.

Particularly, in the case where the total number of substituents is 1, it is preferable that any one of $X^1$, $X^2$, $X^5$ and $X^6$ be —$CH_3$, a fluorine atom or a chlorine atom, and more preferably, —$CH_3$ or a fluorine atom. Furthermore, when one benzene ring has two substituents, and the total number of substituents is two, it is preferable that $X^1$ and $X^2$, or $X^5$ and $X^6$ be fluorine atoms.

Specific examples of the chiral compound A represented by the formula (3) include chiral compounds A represented by the following general formulae (3-1) to (3-4):

[Chemical Formula 10]

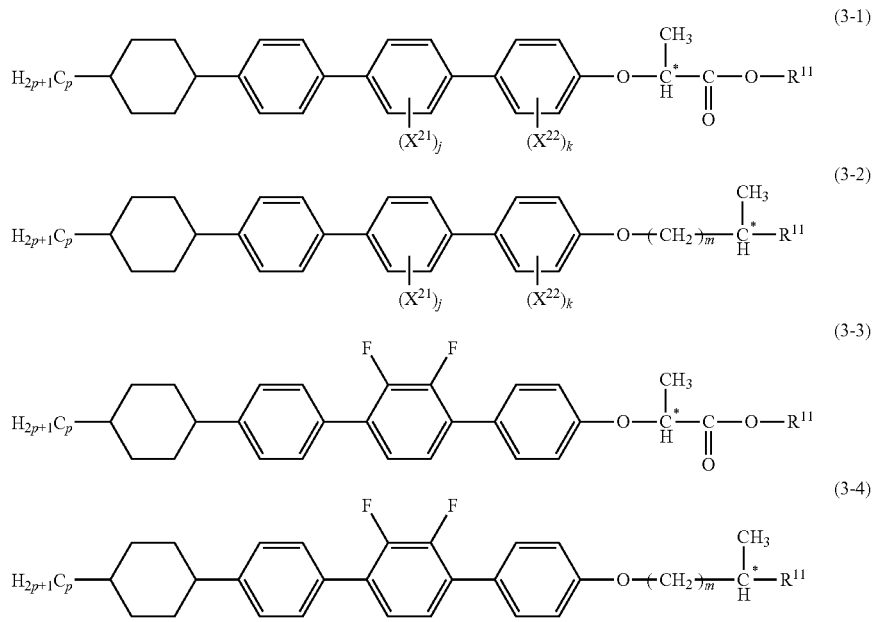

wherein in the formulae (3-1) to (3-4), $R^{11}$ represents a saturated or unsaturated linear, branched or cyclic alkyl group having 1 to 10 carbon atoms, and above all, $R^{11}$ is preferably a linear or branched saturated alkyl group, or a phenylalkyl group. Symbol * represents a chiral center, and "m" represents 0 or 1. "p" is 4 to 18, preferably 6 to 18, and more preferably 6 to 12. In the formulae (3-1) and (3-2), $X^{21}$ and $X^{22}$ each independently represent —$CH_3$, —$CF_3$ or a halogen atom, and among them, —$CH_3$, a fluorine atom or a chlorine atom is preferred. The positions of $X^{21}$ and $X^{22}$ are the same as the positions of $X^1$ to $X^8$ described above. "j" and "k" are such that one of them is 0, while the other is 1.

Specific examples of the chiral compound A represented by the formulae (3-1) to (3-4) include chiral compounds A represented by the following formulae:

TABLE 1

$C_7H_{15}$—[cyclohexyl]—[phenyl]—[phenyl with $X^1, X^2$]—[phenyl with $X^3$]—OR

| $X^1$ | $X^2$ | $X^3$ | R |
|---|---|---|---|
| — | Cl | — | —$C^*H(CH_3)COOC_4H_9$ |
| — | $CH_3$ | — | —$C^*H(CH_3)COOC_4H_9$ |
| — | $CH_3$ | — | —$C^*H(CH_3)C_6H_{13}$ |
| — | Cl | — | —$C^*H(CH_3)COOCH_2CH(CH_3)_2$ |
| — | Cl | — | —$CH_2C^*H(CH_3)C_2H_5$ |
| — | Cl | — | —$C^*H(CH_3)COOC(CH_3)_3$ |
| — | Cl | — | —$C^*H(CH_3)COOCH_2C_6H_5$ |
| — | Cl | — | —$C^*H(CH_3)COOC_2H_5$ |
| — | $CH_3$ | — | —$C^*H(CH_3)COOC_2H_5$ |
| — | $CH_3$ | — | —$C^*H(CH_3)COOC_3H_7$ |
| — | $CH_3$ | — | —$C^*H(CH_3)COOC_6H_{13}$ |
| — | $CH_3$ | — | —$C^*H(CH_3)COOC_8H_{17}$ |
| — | — | $CH_3$ | —$C^*H(CH_3)COOC_2H_5$ |
| F | F | — | —$C^*H(CH_3)COOC_2H_5$ |
| F | F | — | —$C^*H(CH_3)COOC_4H_9$ |

TABLE 1-continued $C_7H_{15}$—[cyclohexyl]—[phenyl]—[phenyl with $X^1, X^2$]—[phenyl with $X^3$]—OR

| $X^1$ | $X^2$ | $X^3$ | R |
|---|---|---|---|
| F | F | — | —$C^*H(CH_3)COOC(CH_3)_3$ |
| — | F | — | —$C^*H(CH_3)COOC_4H_9$ |

Regarding such chiral compounds A, one kind may be used singly, or two or more kinds may be used in mixture.

A chiral compound A can be synthesized by, for example, the method described in the pamphlet of WO 2010/031431.

(2) Chiral Compound B

The chiral compound B that is used in the present invention is a compound represented by the following general formula (4):

[Chemical Formula 11]

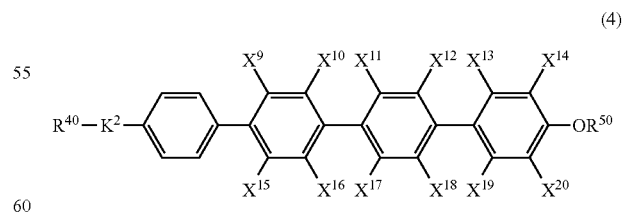

(4)

In the formula (4), $K^2$ represents a single bond or a cyclohexane ring. When $K^2$ is a single bond, as shown in the following general formula (4-1), the chiral compound B becomes a compound in which four benzene rings are directly linked. When $K^2$ is a cyclohexane ring, as shown in the following general formula (4-2), the chiral compound B becomes a compound in which four benzene rings and one cyclohexane ring are directly linked.

Among others, it is preferable that $K^2$ be a single bond.

[Chemical Formula 12]

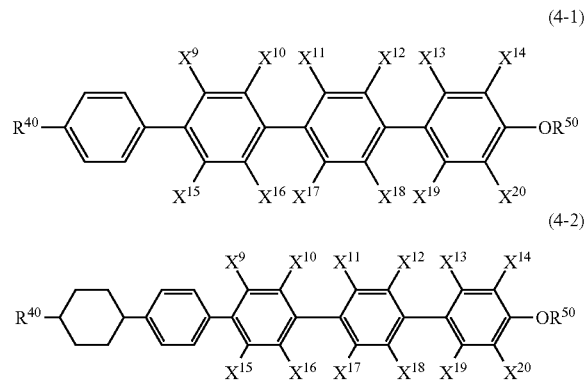

In the formula (4), $R^{40}$ is a non-chiral group and represents a saturated or unsaturated alkyl group or alkoxyalkyl group having 4 to 18 carbon atoms which may be substituted with a halogen atom. Incidentally, since $R^{40}$ has the same meaning as $R^{10}$ in the formula (3), further description will not be repeated here.

In the formula (4), $R^{50}$ is a chiral group having one or more chiral centers and is a group represented by the formula (5). Incidentally, since the group represented by the formula (5) has the same meaning as in the case of the chiral compound A, further description will not be repeated here.

In the formula (4), $X^9$ to $X^{20}$ each independently represent —$CH_3$, —$CF_3$, a halogen atom, or a hydrogen atom. However, one or more of $X^9$ to $X^{20}$ are each independently —$CH_3$, —$CF_3$, or a halogen atom. Incidentally, the reason why one or more of $X^9$ to $X^{20}$ represent —$CH_3$, —$CF_3$ or halogen atoms is the same as in the case of $X^1$ to $X^8$ in the formula (3), and therefore, further description will not be repeated here.

Among others, it is preferable that any one or more of $X^9$ to $X^{13}$ and $X^{15}$ to $X^{19}$ be each independently —$CH_3$, —$CF_3$, or a halogen atom. It is because when the compound has substituents at the positions of $X^9$ to $X^{13}$ and $X^{15}$ to $X^{19}$, the chiral compound has superior solubility than in the case of the positions of $X^{14}$ and $X^{20}$. This is speculated to be because the case of the positions of $X^{14}$ and $X^{20}$ involves less strain caused by substituents as compared with the case of other positions.

Among the three benzene rings to which $X^9$ to $X^{20}$ are bonded, a benzene ring having substituents may have one to four substituents, but above all, it is preferable that the benzene ring have one to two substituents. When one benzene ring has one substituent, the substituent is preferably —$CH_3$, a fluorine atom or a chlorine atom, and more preferably —$CH_3$ or a fluorine atom. Furthermore, when one benzene ring has two substituents, it is preferable that the substituents be all fluorine atoms. In this case, regarding the positions of the two substituents, for the same reason as that in the case of the chiral compound A, for example, it is preferable that adjoining carbon atoms of a benzene ring be each substituted by a fluorine atom, as in the case where $X^{11}$ and $X^{12}$ are fluorine atoms.

Furthermore, it is preferable that the chiral compound represented by the formula (4) have one to two substituents in total.

Moreover, it is preferable that one benzene ring among the benzene rings to which $X^9$ to $X^{20}$ are bonded have substituents, and among others, from the viewpoint of suppressing crystallization, it is preferable that the benzene ring that is located in the middle, specifically, any one of the benzene ring to which $X^9$, $X^{10}$, $X^{15}$ and $X^{16}$ are bonded and the benzene ring to which $X^{11}$, $X^{12}$, $X^{17}$ and $X^{18}$ are bonded, have substituents.

Particularly, in the case where the total number of substituents is 1, any one of $X^9$ to $X^{20}$ is preferably —$CH_3$, a fluorine atom or a chlorine atom, and more preferably —$CH_3$ or a fluorine atom. Furthermore, when one benzene ring has two substituents, and the total number of substituents is two, it is preferable that $X^9$ and $X^{10}$, $X^{11}$ and $X^{12}$, $X^{15}$ and $X^{16}$, or $X^{17}$ and $X^{18}$ be fluorine atoms.

In regard to the formulae (4-1) and (4-2), $R^{40}$, $R^{50}$, and $X^9$ to $X^{20}$ have the same meanings as those in the formula (4)

Specific examples of the chiral compound B represented by the formula (4) include chiral compounds B represented by the following general formulae (4-3) to (4-10):

[Chemical Formula 13]

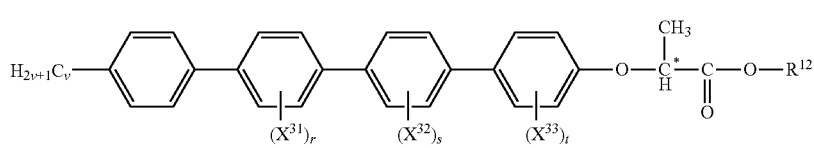

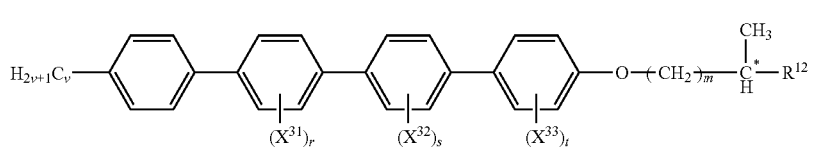

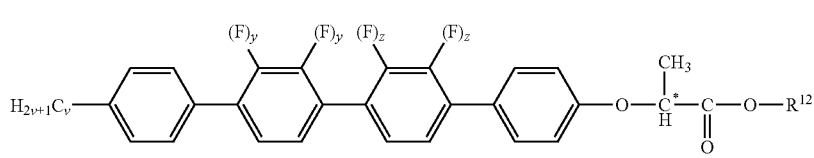

-continued

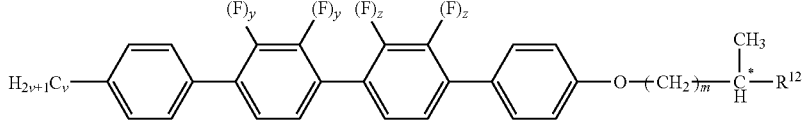
(4-6)

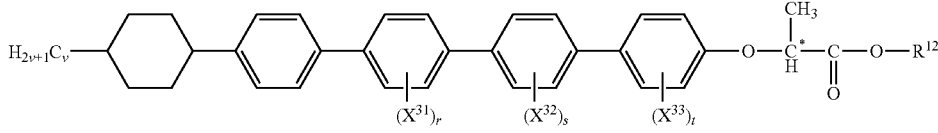
(4-7)

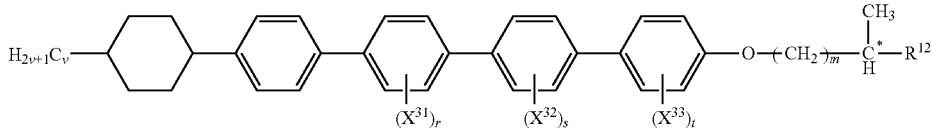
(4-8)

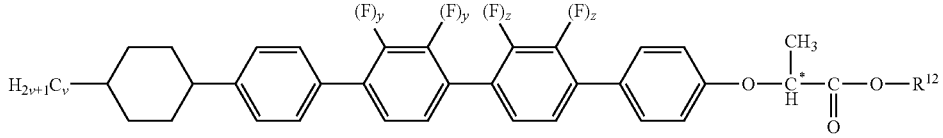
(4-9)

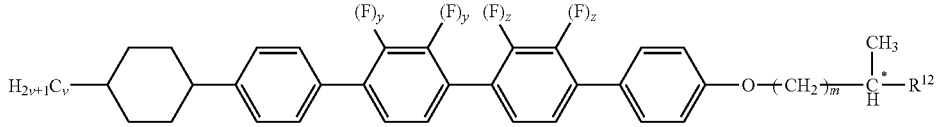
(4-10)

In the formulae (4-3) to (4-10), $R^{12}$ represents a saturated or unsaturated linear, branched or cyclic alkyl group having 1 to 10 carbon atoms, and above all, $R^{12}$ is preferably a saturated linear or branched alkyl group, or a phenylalkyl group. Symbol * represents a chiral center, "m" represents 0 or 1, and the carbon atom at the 1-position or the 2-position serves as the chiral center. "v" represents 4 to 18, preferably 6 to 0.18, and more preferably 6 to 12. In the formulae (4-3), (4-4), (4-7) and (4-8), $X^{31}$ to $X^{33}$ each independently represent —$CH_3$, —$CF_3$ or a halogen atom, and among them, —$CH_3$, a fluorine atom or a chlorine atom is preferred. The positions of $X^{31}$ to $X^{33}$ are the same as the positions of $X^9$ to $X^{20}$ described above. "r", "s" and "t" are such that any one or two of them are 1, and the other is 0. In the formulae (4-5), (4-6), (4-9) and (4-10), one of "y" and "z" is 1, and the other is 0.

Specific examples of the chiral compound B represented by the formulae (4-3) to (4-10) include chiral compounds B represented by the following formulae:

TABLE 2

| v | k | $X^1$ | $X^2$ | $X^3$ | $X^4$ | R |
|---|---|---|---|---|---|---|
| 6 | 0 | — | — | Cl | — | —C*H($CH_3$)$C_6H_{13}$ |
| 7 | 0 | — | — | Cl | — | —C*H($CH_3$)$C_6H_{13}$ |
| 8 | 0 | — | — | Cl | — | —C*H($CH_3$)$C_6H_{13}$ |
| 10 | 0 | — | — | Cl | — | —C*H($CH_3$)$C_5H_{13}$ |
| 8 | 0 | — | — | Cl | — | —C*H($CH_3$)$C_5H_{13}$ |
| 8 | 0 | — | — | $CH_3$ | — | —C*H($CH_3$)$C_5H_{13}$ |
| 6 | 0 | $CH_3$ | — | — | — | —C*H($CH_3$)$C_6H_{13}$ |
| 6 | 0 | Cl | — | — | — | —C*H($CH_3$)$C_6H_{13}$ |
| 8 | 0 | — | — | F | — | —C*H($CH_3$)$C_6H_{13}$ |
| 8 | 0 | — | F | F | — | —C*H($CH_3$)$C_6H_{13}$ |
| 8 | 0 | — | — | Cl | — | —C*H($CH_3$)COO$C_2H_5$ |
| 6 | 0 | — | — | $CH_3$ | — | —C*H($CH_3$)COO$C_2H_5$ |
| 8 | 0 | — | — | $CH_3$ | — | —C*H($CH_3$)COO$C_4H_9$ |
| 8 | 0 | — | — | $CH_3$ | — | —C*H($CH_3$)COO$CH_2$CH($CH_3$)$_2$ |
| 8 | 0 | — | — | $CH_3$ | — | —C*H($CH_3$)COO$C_2H_5$ |
| 8 | 0 | — | — | $CH_3$ | — | —C*H($CH_3$)COO$CH_2$C($CH_3$)$_3$ |
| 8 | 0 | — | — | $CH_3$ | — | —C*H($CH_3$)COO$CH_2$$C_6H_5$ |

TABLE 2-continued $C_vH_{2v+1}$—[(cyclohexane)]$_k$—(benzene)—(benzene)—(benzene with $X^1$, $X^2$)—(benzene with $X^3$)—(benzene with $X^4$)—OR

| v | k | $X^1$ | $X^2$ | $X^3$ | $X^4$ | R |
|---|---|---|---|---|---|---|
| 8 | 0 | — | — | — | $CH_3$ | —$C*H(CH_3)COOC_2H_5$ |
| 8 | 0 | — | — | $CH_3$ | $CH_3$ | —$C*H(CH_3)COOC_2H_5$ |
| 8 | 0 | — | — | F | — | —$C*H(CH_3)COOC_2H_5$ |
| 8 | 0 | — | F | F | — | —$C*H(CH_3)COOC_2H_5$ |
| 7 | 1 | — | — | $CH_3$ | — | —$C*H(CH_3)COOC_2H_5$ |
| 7 | 1 | — | — | Cl | — | —$C*H(CH_3)COOC_2H_5$ |
| 7 | 1 | — | — | $CH_3$ | — | —$C*H(CH_3)C_6H_{13}$ |

Regarding such chiral compounds B, one kind may be used singly, or two or more kinds may be used in mixture.

For example, a ferroelectric liquid crystal composition may contain a chiral compound B represented by the formula (4-1) and a chiral compound B represented by the formula (4-2).

A chiral compound B can be synthesized by, for example, the method described in the pamphlet of WO 2010/031431.

(3) Chiral Compound A and Chiral Compound B

When the ferroelectric liquid crystal composition of the present invention contains at least one of the chiral compound A and the chiral compound B, the liquid crystal composition may contain only the chiral compound A, may contain only the chiral compound B, or may contain the chiral compound A and the chiral compound B. Furthermore, when the ferroelectric liquid crystal composition contains the chiral compound A, the liquid crystal composition may contain one kind of a chiral compound A, or may contain two or more kinds of chiral compounds A. Similarly, when the ferroelectric liquid crystal composition contains the chiral compound B, the liquid crystal composition may contain one kind of a chiral compound B, or may contain two or more kinds of chiral compounds B.

Particularly, the ferroelectric liquid crystal composition of the present invention preferably contains a chiral compound A and a chiral compound. B. Furthermore, it is also preferable that the ferroelectric liquid crystal composition of the present invention contain a chiral compound. B1 represented by the formula (4-1) in which four benzene rings are directly bonded to each other, and a chiral compound B2 represented by the formula (4-2) in which four benzene rings and one cyclohexane ring are directly bonded to each other. It is because when the ferroelectric liquid crystal composition contains such two kinds of chiral compounds, impact resistance can be effectively enhanced.

When the ferroelectric liquid crystal composition of the present invention contains only a chiral compound A, the content of the chiral compound A in the ferroelectric liquid crystal composition is not particularly limited as long as the content can provide an effect of impact resistance. In the case of using one kind of the chiral compound A alone, the content of the chiral compound A described above is preferably 5% by mass or more in the ferroelectric liquid crystal composition, and in the case of mixing two or more kinds of the chiral compounds A described above, the content of each of the two or more kinds of chiral compounds A is preferably 5% by mass or more in the ferroelectric liquid crystal composition. Above all, in the case of using one kind of the chiral compound A alone, the content of the chiral compound A is preferably in the range of 5% by mass to 35% by mass, and more preferably in the range of 15% by mass to 30% by mass, in the ferroelectric liquid crystal composition, while in the case of mixing two or more kinds of the chiral compounds A, the total content of the two or more kinds of the chiral compounds A is preferably in the range of 5% by mass to 35% by mass, and more preferably in the range of 15% by mass to 30% by mass, in the ferroelectric liquid crystal composition. It is because if the content of the chiral compound A is smaller than the range described above, desired impact resistance may not be obtained. On the other hand, if the content of the chiral compound A is larger than the range described above, the ferroelectric liquid crystal composition may have an increased viscosity or may be easily crystallized, sufficient impact resistance may not be obtained. Also, at the time of producing a liquid crystal display device, it may be difficult to form a liquid crystal layer.

When the ferroelectric liquid crystal composition of the present invention contains only a chiral compound B, the content of the chiral compound B in the ferroelectric liquid crystal composition is not particularly limited as long as the content level can provide an effect of impact resistance, and is the same as the content of the chiral compound A.

When the ferroelectric liquid crystal composition of the present invention contains a chiral compound A and a chiral compound B, the total content of the chiral compound A and the chiral compound B in the ferroelectric liquid crystal composition is not particularly limited as long as the content level can provide an effect of impact resistance, and is the same as the content of the chiral compound A.

Furthermore, when the ferroelectric liquid crystal composition of the present invention contains a chiral compound A and a chiral compound B, the content of the chiral compound B in the ferroelectric liquid crystal composition is preferably greater than or equal to the content of the chiral compound A. It is because the chiral compound A tends to decrease the tilt angle of the liquid crystal molecules at the time when a voltage is applied, as compared with the chiral compound B. Therefore, if the content of the chiral compound A is made larger compared to the chiral compound. B, the tilt angle of the liquid crystal molecules is made small, and there is a risk that sufficient brightness may not be obtained. On the contrary, as the chiral compound B is contained in a larger amount as compared with the chiral compound A, the tilt angle of the liquid crystal molecules can be made larger, and the drive performance can be enhanced.

3. Host liquid crystal

The ferroelectric liquid crystal composition of the present invention may further contain a host liquid crystal.

As the host liquid crystal, liquid crystals that are generally used as host liquid crystals of ferroelectric liquid crystal compositions can be used, and examples thereof include phenylpyrimidine compounds.

Here, since a phenylpyrimidine compound has at least two aromatic rings such as a benzene ring and a pyrmidine ring at the core section, birefringence is prone to increase. However, in the present invention, since a birefringence improving agent represented by the formula (1) is contained, the birefringence of the ferroelectric liquid crystal composition can be made small.

Regarding the host liquid crystal, one kind may be used alone, or two or more kinds may be used in mixture.

The content of the host liquid crystal in the ferroelectric liquid crystal composition is not particularly limited as long as the contents of the chiral compounds can be adjusted to the ranges described above.

4. Ferroelectric liquid crystal composition

The ferroelectric liquid crystal composition of the present invention is not particularly limited as long as the liquid crystal composition is capable of exhibiting the chiral smectic C (SmC*) phase. Examples of the phase sequence of the ferroelectric liquid crystal composition include phase transition of the nematic (N) phase-cholesteric (Ch) phase-SmC* phase, phase transition of N phase-SmC* phase, phase transition of N phase-smectic A (SmA) phase-SmC* phase, and phase transition of N phase-Ch phase-SmA phase-SmC* phase, in a temperature lowering process.

Furthermore, regarding the ferroelectric liquid crystal composition, a ferroelectric liquid crystal composition exhibiting bistability and a ferroelectric liquid crystal composition exhibiting monostability can all be used. Among them, a ferroelectric liquid crystal composition exhibiting monostability is preferred. It is because when a ferroelectric liquid crystal composition exhibiting monostability is used, a gradation display is enabled by continuously changing the director (gradient of the molecular axis) of the liquid crystal by means of voltage change, and thereby analogously modulating the intensity of light transmission. Particularly, in the case of driving a liquid crystal display device by a field sequential color mode, it is preferable to use a ferroelectric liquid crystal composition which exhibits monostability. It is because when a ferroelectric liquid crystal composition exhibiting monostability is used, driving by the active matrix mode using a TFT is enabled, gradation control is also enabled by voltage modulation, and a high definition and high resolution display can be realized.

Incidentally, the term "exhibiting monostability" means a state in which the state of liquid crystal molecules without voltage application is stabilized in a single state. A ferroelectric liquid crystal composition is such that as illustrated in FIG. 1, liquid crystal molecules 25 are inclined from the layer normal line z, and rotate along the ridge line of a cone having a bottom surface that is perpendicular to the layer normal line z. In such a cone, the inclination angle of the liquid crystal molecules 25 with respect to the layer normal line z is called a tilt angle θ. As such, liquid crystal molecules 25 can be operated on the cone between two states that are inclined by the (tilt angle±θ) with respect to the layer normal line z. To specifically explain, exhibiting monostability means a state in which when no voltage is applied, liquid crystal molecules 25 are stabilized in any one state on the cone.

Furthermore, the ferroelectric liquid crystal composition is desirably a liquid crystal composition exhibiting monostability, and a ferroelectric liquid crystal composition exhibiting half V-shaped switching characteristics in which liquid crystal molecules operate only when any of a positive voltage or a negative voltage is applied; a ferroelectric liquid crystal composition exhibiting V-shaped switching characteristics in which liquid crystal molecules operate to the same extent at any of a positive voltage or a negative voltage; and a ferroelectric liquid crystal composition exhibiting asymmetric switching characteristics in which the operation of liquid crystal molecules at any of a positive voltage or a negative voltage becomes larger as compared with the operation of liquid crystal molecules at a voltage of the other polarity, can all be used.

As such a ferroelectric liquid crystal composition, various liquid crystal compositions can be selected among those generally known liquid crystal materials in accordance with the required characteristics. Particularly, a ferroelectric liquid crystal composition which exhibits the SmC* phase from the Ch phase without going through the SmA phase, is preferred because the change in the operation characteristics with voltage is small against temperature changes.

C. Liquid crystal display device

The liquid crystal display device of the present invention comprises a first alignment treatment substrate comprising a first base material, a first electrode layer formed on the first base material, and a first alignment layer formed on the first electrode layer; a second alignment treatment substrate comprising a second base material, a second electrode layer formed on the second base material, and a second alignment layer formed on the second electrode layer; and a liquid crystal layer that is formed between the first alignment layer and the second alignment layer and contains the ferroelectric liquid crystal composition described above.

The liquid crystal display device of the present invention will be described with reference to the drawings.

Figure 2:
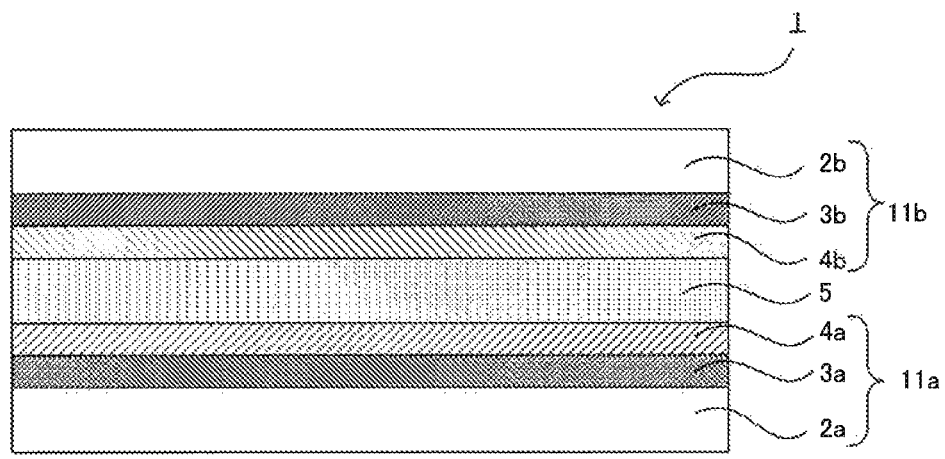
FIG. 2 is a schematic cross-sectional diagram illustrating an example of the liquid crystal display device of the present invention.

FIG. 2 is a cross-sectional diagram illustrating an example of the liquid crystal display device of the present invention. As illustrated in FIG. 2, the liquid crystal display device 1 comprises a first alignment treatment substrate 11a comprising a first base material 2a, a first electrode layer 3a formed on the first base material 2a, and a first alignment layer 4a formed on the first electrode layer 3a; a second alignment treatment substrate 11b comprising a second base material 2b, a second electrode layer 3b formed on the second base material 2b, and a second alignment layer 4b formed on the second electrode layer 3b; and a liquid crystal layer 5 that is formed between the first alignment layer 4a and the second alignment layer 4b and contains the ferroelectric liquid crystal composition described above.

According to the present invention, since the ferroelectric liquid crystal composition contains a birefringence improving agent represented by the formula (1), the birefringence of the ferroelectric liquid crystal composition can be reduced, and a satisfactory white display can be obtained. Furthermore, when the ferroelectric liquid crystal composition contains a chiral compound that improves impact resistance, impact resistance can be maintained.

Hereinafter, various constituents of the liquid crystal display device of the present invention will be described.

1. Liquid crystal layer

The liquid crystal layer according to the present invention is a layer that is formed between the first alignment layer of the first alignment treatment substrate and the second alignment layer of the second alignment treatment substrate and contains the ferroelectric liquid crystal composition described above.

Incidentally, since the ferroelectric liquid crystal composition has been described in detail in the section "B. Ferroelectric liquid crystal composition", further description will not be repeated here.

The thickness of the liquid crystal layer is preferably in the range of 2.0 µm to 10.0 µm, more preferably in the range of 2.3 µm to 5.0 µm, and even more preferably in the range of 2.5 µm to 3.5 µm. It is because if the thickness of the liquid crystal layer is too thin, there is a risk that defects may become highly conspicuous as a result of incorporation of foreign materials at the time of production. On the contrary, if the thickness of the liquid crystal layer is too thick, it becomes difficult for the liquid crystal molecules to align themselves, and there is a possibility that the contrast may decrease. The thickness of the liquid crystal layer can be adjusted by a bead spacer, a columnar spacer, a partition or the like.

Regarding the method for forming the liquid crystal layer, a method that is generally used as a method for producing a liquid crystal cell can be used, and for example, a vacuum injection system, or a liquid crystal dropwise addition system can be used.

When the ferroelectric liquid crystal composition is aligned, it is preferable to perform slow cooling, and it is not necessary to apply a voltage to the liquid crystal layer.

2. First alignment treatment substrate

The first alignment treatment substrate that is used in the present invention comprises a first base material, a first electrode layer formed on the first base material, and a first alignment layer formed on the first electrode layer.

Hereinafter, various constituents of the first alignment treatment substrate will be described.

(1) First alignment layer

The first alignment layer used in the present invention is not particularly limited as long as the first alignment layer is capable of the controlling alignment of the ferroelectric liquid crystal composition, and examples thereof include a photo alignment layer, a rubbing alignment layer, and an oblique evaporation alignment layer. Hereinafter, these alignment layers will be explained.

(a) Photo alignment layer

The photo-excitation reactions used in the formation of a photo alignment layer can be roughly divided into photoreactions and photo-isomerization reactions. Furthermore, examples of the photoreactions include photo-dimerization reactions and photo-decomposition reactions.

Regarding the material, forming method and thickness of the photo alignment layer, general materials, forming methods and thicknesses can be applied, and for example, those described in JP-A No. 2006-350322, JP-A No. 2006-323214, JP-A No. 2005-258429, and JP-A No. 2005-258428 can be used.

(b) Rubbing Alignment Layer

Regarding the material, forming method and thickness of the rubbing alignment layer, general materials, forming methods and thicknesses can be applied.

(c) Compositions of constituent materials of first alignment layer and second alignment layer In the present invention, it is preferable that the constituent materials of the first alignment layer and the constituent materials of the second alignment layer have compositions that are different from each other, with a liquid crystal layer interposed therebetween. When the first alignment layer and the second alignment layer are formed using materials having compositions that are different from each other, the polarities of the first alignment layer surface and the second alignment layer surface can be made different in accordance with the respective materials. Thereby, the polar surface interaction between the ferroelectric liquid crystal composition and the first alignment layer and the polar surface interaction between the ferroelectric liquid crystal composition and the second alignment layer become different from each other. Therefore, when the materials are appropriately selected by considering the surface polarities of the first alignment layer and the second alignment layer, the occurrence of alignment defects such as zigzag defects, hairpin defects, and two kinds of domains in which the stabilization states of liquid crystal molecules without voltage application are different, can be suppressed. As a result, the contrast can be enhanced.

In order to make the constituent materials of the first alignment layer and the second alignment layer to have compositions that are different from each other, with the liquid crystal layer interposed therebetween, for example, it is preferable to have a photo alignment layer on one side, and a rubbing alignment layer on the other side.

Furthermore, for example, it is preferable to have rubbing alignment layers on both sides, with different compositions of the constituent materials of the rubbing alignment layers; or to have photo alignment layers on both sides, with different compositions of the constituent materials of the photo alignment layers.

When the first alignment layer and the second alignment layer are rubbing alignment layers, the compositions can be varied by changing the main chain, substituent or side chain, or changing the amount of addition of an additive, or by means of the presence or absence of an additive.

Furthermore, when the first alignment layer and the second alignment layer are photo alignment layers, the compositions of the constituent materials of the photo alignment layers can be made different by, for example, using a photo-isomerization type material in the photo alignment layer on one side, while using a photoreaction type material in the photo alignment layer on the other side.

Furthermore, when the first alignment layer and the second alignment layer are photo alignment layers using photo-isomerization type materials, the composition can be varied by changing the isomerization site, substituent, side chain or the like, using a monomolecular compound and a polymerizable monomer respectively, or changing the amount of addition of an additive, or by means of the presence or absence of an additive.

Also, when the first alignment layer and the second alignment layer are photo alignment layers using photo-dimerization type materials, the composition can be varied by changing the dimerization reaction site, substituent, side chain or the like, or changing the amount of addition of an additive, or by means of the presence or absence of an additive.

(2) First electrode layer

The first electrode layer that is used in the present invention is not particularly limited as long as it is an electrode that is generally used as an electrode for a liquid crystal display device.

(3) First base material

The first base material that is used in the present invention is not particularly limited as long as it is an electrode that is generally used as a base material for a liquid crystal display device, and preferred examples include a glass plate and a plastic plate.

(4) Other constituents

According to the present invention, a partition or a columnar spacer may be formed on the first base material or the second base material. As the partition and the columnar spacer, general partitions and columnar spacers can be applied.

Furthermore, in the present invention, colored layers may be formed on the first base material or the second base material. In the case where colored layers are formed, a liquid crystal display device of a color filter system in which a color display can be realized by means of colored layers, can be obtained. As the colored layers, general colored layers can be applied.

3. Second alignment treatment substrate

The second alignment treatment substrate that is used in the present invention comprises a second base material, a second electrode layer formed on the second base material, and a second alignment layer formed on the second electrode layer.

Incidentally, the second base material, second electrode layer, second alignment layer and other constituents are the same as the first base material, first electrode layer, first alignment layer and other constituents in the first alignment treatment substrate, respectively, and further description will not be repeated here.

4. Method for driving liquid crystal display device

Regarding the method for driving a liquid crystal display device of the present invention, since the rapid response properties of a ferroelectric liquid crystal composition can be utilized, in order to perform time-sharing of one pixel and to obtain satisfactory dynamic image display characteristics, a field sequential color system that requires rapid response properties in particular can also be suitably used.

Furthermore, the method for driving a liquid crystal display device of the present invention is not limited to a field sequential system, and a color filter system which implements a color display using colored layers may also be employed.

As the method for driving a liquid crystal display device of the present invention, an active matrix system using a thin film transistor (TFT) is preferred. It is because when an active matrix system using a TFT is employed, intended pixels can be reliably lighted on and lighted off, and therefore, a high quality display can be achieved.

Furthermore, the method for driving a liquid crystal display device of the present invention may also be a segment system.

D. Compound

The compound of the present invention has a structure represented by the following general formula (2):

[Chemical Formula 14]

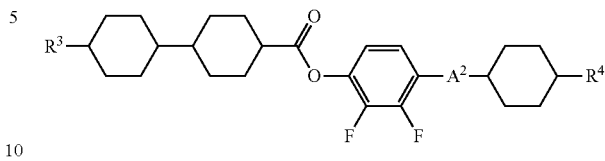

(2)

wherein in the formula (2), $R^3$ and $R^4$ each represent a linear or branched alkyl group having 3 to 9 carbon atoms, provided that at least one of $R^3$ and $R^4$ has 5 or more carbon atoms; and $A^2$ represents —O—$CH_2$— or —$CH_2$—O—.

That is, the compound of the present invention is represented by the following general formulae (2-1) and (2-2):

[Chemical Formula 15]

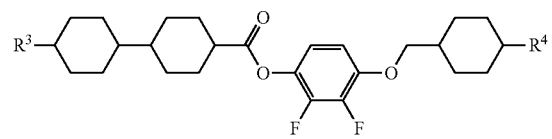

(2-1)

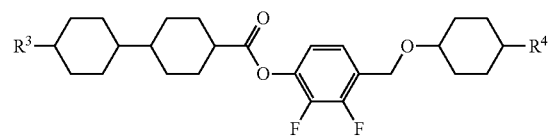

(2-2)

wherein in the formulae (2-1) and (2-2), $R^3$ and $R^4$ have the same meanings as $R^3$ and $R^4$ in the formula (1), respectively.

When the compound of the present invention has a structure represented by the formula (2), similarly to the birefringence improving agent represented by the general formula (1), in the case where the compound is added to a ferroelectric liquid crystal composition, birefringence can be reduced. Also, in a liquid crystal display device in which the ferroelectric liquid crystal composition is used, even if the cell gap is relatively large, the occurrence of color shift is suppressed, and a satisfactory white display can be realized.

1. Compounds represented by formulae (2-1) and (2-2)

In the formulae (2-1) and (2-2), $R^3$ and $R^4$ have the same meanings as $R^1$ and $R^2$ in the general formulae (1-1) to (1-3) described above, respectively, and thus further description will not be repeated here.

Specific examples of the compounds represented by the formulae (2-1) and (2-2) include compounds represented by the following formulae:

[Chemical Formula 16]

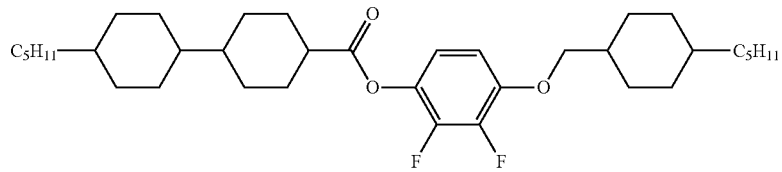

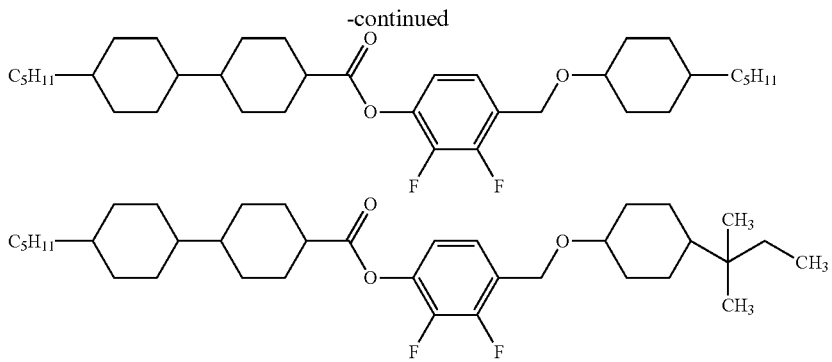

2. Synthesis method

The compound of the present invention can be synthesized from an arbitrary raw material compound by using a generally known organic synthesis method. Incidentally, since the method for synthesizing the compound of the present invention is the same as the synthesis method for the general formula (1) described above, further description will not be repeated here.

3. Use

The use of the compound represented by the formula (2) is not particularly limited, but the compound is suitably used as a birefringence improving agent for a ferroelectric liquid crystal composition. As the compound represented by the formula (2) is incorporated into the ferroelectric liquid crystal composition, when the ferroelectric liquid crystal composition is used in a liquid crystal display device, the occurrence of color shift is suppressed while the drive performance is maintained, and a satisfactory white display can be obtained.

Here, in the case where a ferroelectric liquid crystal composition containing the compound represented by the formula (2) is used in a liquid crystal display device, the compound represented by the formula (2) is such that one kind may be used alone, or two or more kinds may be used in mixture.

Incidentally, the present invention is not intended to be limited to the embodiment described above. The above-described embodiment is for illustrative purposes, and any embodiment that has substantially the same constitution as the technical idea described in the claims of the present invention and provides the same operating effect, is intended to be included in the technical scope of the present invention.

EXAMPLES

Hereinafter, the present invention will be described in more detail by way of Examples and Comparative Examples.

Example 1

First, under the conditions of a nitrogen atmosphere, 40 ml of anhydrous THF was provided, and 1.57 g (41.4 mmol) of LiAlH$_4$ was added to the anhydrous THF that was ice-cooled, and the mixture was stirred for 15 minutes. To the mixture, a solution of 5.5 g (27.7 mmol) of 4-trans-pentylcyclohexanecarboxylic acid dissolved in 20 ml of anhydrous THF was added dropwise over 15 minutes, and thereafter, the mixture was returned to room temperature and stirred for 2 hours. Next, 4 ml of water and 4.5 ml of a 15% aqueous solution of NaOH were added to the solution, and the resulting mixture was stirred for 20 minutes. Insoluble materials were removed by performing Celite filtration. Subsequently, the filtrate obtained by Celite filtration was extracted with ethyl acetate, and the organic layer was washed with saturated saline and water. Thereafter, the organic layer was dried over MgSO$_4$, concentrated, and dried under reduced pressure, and thereby colorless, oily 4-trans-n-pentylcyclohexanemethanol was obtained. The amount of the compound thus obtained was 5.1 g, and the yield was 100%.

Under the conditions of a nitrogen atmosphere, a solution was prepared by dissolving 2.5 g (19.2 mmol) of 2,3-difluorophenol and 3.9 g (21.2 mmol) of 4-trans-n-pentylcyclohexanemethanol in 40 ml of anhydrous THF, and 11.1 g (42.3 mmol) of triphenylphosphine was added thereto. The mixture was ice-cooled. To the mixture, 8.6 g (42.5 mmol) of diisopropyl azodicarboxylate was added dropwise over 30 minutes, and the mixture was stirred for 2 hours. Thereafter, the mixture was returned to room temperature and stirred for 12 hours, and this solution was extracted with ethyl acetate. The organic layer was washed with a dilute aqueous hydrochloric acid solution and water. Thereafter, the organic layer was dried over MgSO$_4$ and concentrated, and thereby a yellow oily substance was obtained. Subsequently, N-hexane was added to the oily substance, a white solid precipitated therefrom at this time was removed by filtration, and the filtrate was concentrated. Thereafter, the residue thus obtained was purified by silica gel column chromatography (developer liquid: N-hexane), and thereby 4-trans-n-pentyl-1-(2,3-difluorophenoxymethyl)cyclohexane as a white solid was obtained. The amount of the compound thus obtained was 4.1 g, and the yield was 71.9%.

Under the conditions of an Ar atmosphere, a solution prepared by dissolving 4.0 g (13.5 mmol) of 4-trans-n-pentyl-1-(2,3-difluorophenoxymethyl)cyclohexane in 20 ml of anhydrous THF was stirred at or below −40° C., and 10 ml of a 1.6 M butyllithium hexane solution (16 mmol) was added dropwise thereto over 1.5 minutes. The mixture was stirred for 4 hours. Next, to the solution thus obtained, 1.68 g (16.2 mmol) of trimethoxyborane was added dropwise over 10 minutes, and the resulting mixture was stirred for 12 hours. Next, this solution was returned to room temperature, and a dilute aqueous hydrochloric acid solution was added thereto to acidify the solution. The resulting mixture was stirred for 24 hours, and this solution was extracted with ethyl acetate. The organic layer was dried over MgSO$_4$ and concentrated under reduced pressure. Thereafter, N-hexane was added to the residue thus obtained, the mixture was ice-cooled, and crystals precipitated therefrom were collected by filtration. Thereby, 4-(4-trans-n-pentylcyclohexylmethyloxy)-2,3-difluorophenylboronic acid as a white powder was obtained. The amount of the compound thus obtained was 3.0 g, and the yield was 65.3%.

15 ml of acetic acid was added to 3.0 g (8.8 mmol) of 4-(4-trans-n-pentylcyclohexylmethyloxy)-2,3-difluorophenylboronic acid, and then 1.5 ml of a 30% aqueous hydrogen peroxide solution was slowly added thereto at room temperature. Next, this solution was stirred for 2 hours, water was added thereto, and crystals precipitated therefrom were collected by filtration. Thereby, 4-(4-trans-n-pentylcyclohexylmethyloxy)-2,3-difluorophenol as a pale yellow powder was obtained. The amount of the compound thus obtained was 2.7 g, and the yield was 98%.

Under the conditions of a nitrogen atmosphere, 0.5 g of triethylamine was added to a solution prepared by dissolving 1.1 g (3.5 mmol) of 4-(4-trans-n-pentylcyclohexylmethyloxy)-2,3-difluorophenol in 20 ml of anhydrous methylene chloride, and the mixture was ice-cooled. To this solution, a solution prepared by dissolving 1.26 g (4.2 mmol) of 4-trans-4-(trans-4-n-pentylcyclohexyl)cyclohexylcarbonyl chloride in 5 ml of methylene chloride was added dropwise over 13.5 minutes, and the mixture was stirred for 20 minutes. Next, this solution was returned to room temperature and stirred for one hour, a dilute aqueous hydrochloric acid solution and methylene chloride were added thereto, and the mixture was extracted. Subsequently, the organic layer was washed with water, dried over $MgSO_4$, and concentrated under reduced pressure. Thereafter, methanol was added to the residue thus obtained, the mixture was stirred for one hour at room temperature, and crystals precipitated therefrom were collected by filtration. Thereby, a birefringence improving agent represented by the following formula as a white solid was obtained as a final product. The compound thus obtained was 1.7 g, and the yield was 84.1%.

[Chemical Formula 17]

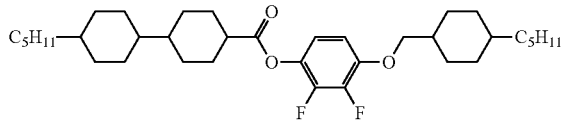

The $^1$H-NMR results for the birefringence improving agent represented by the above formula thus obtained were as follows:

$^1$H-NMR (400 MHz, $CDCl_3$, TMS): δ (ppm) 0.83-1.305 (m, 37H, $CH+CH_2+CH_3$), 1.49-1.585 (m, 2H, $CH_2$), 1.70-1.90 (m, 10H, $CH_2$), 2.14-2.17 (m, 2H, $CH_2$), 2.45-2.53 (m, 1H, CHCO), 3.80 (d, J=6.4 Hz, 2H, $ArOCH_2$), 6.64-6.69 (m, 1H, arom. H), 6.74-6.78 (m, 1H, arom. H)

Example 2

First, in the presence of 4.45 ml (37.414 mmol) of benzyl bromide, 5.016 g (38.557 mmol) of 2,3-difluorophenol and 6.421 g (46.460 mmol) of potassium carbonate were added to 30 ml of DMF, and the mixture was stirred for 1.5 hours at 90° C. in an Ar atmosphere. Next, the mixture was extracted with 50 ml of dichloromethane and 30 ml of water, and the dichloromethane layer was washed two times with 300 ml of water. Thereafter, the dichloromethane layer was dried over $MgSO_4$ and filtered, and the filtrate obtained after filtration was concentrated and dried under reduced pressure. Thereby, oily 2,3-difluorophenyl benzyl ether was obtained. The amount of the compound thus obtained was 8.079 g, and the yield was 95.1%.

Under the conditions of an Ar atmosphere, 8.066 g (36.627 mmol) of 2,3-difluorophenyl benzyl ether was added to 30 ml of THF, and the mixture was stirred at or below −40° C. 24 ml (39.60 mmol) of a 1.65 M butyllithium hexane solution was added dropwise thereto. Subsequently, this solution was stirred for 3 hours, and then dry ice was added, thereto, and the mixture was stirred overnight. Subsequently, the mixture was extracted with 100 ml of dichloromethane, 300 ml of water, and 5 ml of concentrated hydrochloric acid, and the organic layer was dried over $MgSO_4$ and filtered. The filtrate obtained after filtration was concentrated and recrystallized from dichloromethane-hexane. Thereby, 4-benzyloxy-2,3-difluorobenzoic acid as a white solid was obtained. The amount of the compound thus obtained as 2.978 g, and the yield was 30.8%.

Under the conditions of an Ar atmosphere, 2.508 g (9.492 mmol) of 4-benzyloxy-2,3-difluorobenzoic acid was added to 15 ml of THF and 7.5 ml of trimethoxyborane, and the mixture was stirred under ice cooling. Next, to this solution, 10 ml (20 mmol) of a 2 M THF solution of a borane-dimethyl sulfide complex was added dropwise, and the mixture was stirred overnight at room temperature. Thereafter, this solution was poured into 200 ml of ice water, and a precipitate thus obtained was collected by filtration and dried under reduced pressure. Thereby, 4-benzyloxy-2,3-difluorobenzyl alcohol as a white solid was obtained. The amount of the compound thus obtained was 2.262 g, and the yield was 95.2%.

Under the conditions of an Ar atmosphere, 2.257 g (9.019 mmol) of 4-benzyloxy-2,3-difluorobenzyl alcohol was added to 20 ml of dichloromethane, and the mixture was stirred at room temperature. To this solution, 11 ml (11 mmol) of a 1 M dichloromethane solution of phosphorus tribromide was added dropwise, and the mixture was stirred overnight at room temperature. Subsequently, 100 ml of ice water was poured thereto, and the mixture was separated. Thereafter, the organic layer was washed with 300 ml of water, dried over $MgSO_4$, and filtered. The filtrate obtained after filtration was concentrated and dried under reduced pressure. Thereby, 4-benzyloxy-2,3-difluorobenzyl bromide as a white solid was obtained. The amount of the compound thus obtained was 2.562 g, and the yield was 90.7%.

Under the conditions of an Ar atmosphere, 2.573 g (8.217 mmol) of 4-benzyloxy-2,3-difluorobenzyl bromide, 1.400 g (8.221 mmol) of trans-pentylcyclohexanol, and 0.551 g of sodium hydride (60% in oil) (0.331 g (13.776 mmol) of sodium hydride) were added to 15 ml of THF and 5 ml of DMF. The mixture was stirred overnight under the conditions of 60° C. Next, this solution was extracted with 30 ml of dichloromethane and 300 ml of water, and the organic layer was washed two times with 300 ml of water, dried over $MgSO_4$, and filtered. The filtrate obtained after filtration was concentrated. Thereafter, the residue thus obtained was purified by silica gel column chromatography (developer liquid: dichloromethane), and thereby, 2,3-difluoro-4-(trans-pentylcyclohexyl)oxymethylphenyl benzyl ether as a white solid was obtained. The amount of the compound thus obtained was 2.799 g, and the yield was 84.6%.

Under the conditions of a hydrogen atmosphere, 2.775 g (6.893 mmol) of 2,3-difluoro-4-(trans-pentylcyclohexyl)oxymethylphenyl benzyl ether, 0.550 g of 10% palladium carbon, and three droplets of concentrated hydrochloric acid were added to 5 ml of THF and 10 ml of ethanol. The mixture was stirred overnight under the conditions of 60° C. and filtered. Thereafter, the residue obtained by concentration was purified by silica gel column chromatography (developer liquid: dichloromethane), and thereby, 2,3-difluoro-4-(trans-pentylcyclohexyl)oxymethylphenol as a white solid was obtained. The amount of the compound thus obtained was 1.393 g, and the yield was 64.7%.

Under the conditions of an Ar atmosphere, 0.399 g (1.277 mmol) of 2,3-difluoro-4-(trans-pentylcyclohexyl)oxymethylphenol, 0.432 g (1.445 mmol) of trans, trans-4-(4'-pentylcyclohexyl)cyclohexylcarbonyl chloride, and 0.27 ml of triethylamine were added to 10 ml of dichloromethane, and the mixture was stirred overnight at room temperature. Incidentally, the trans, trans-4-(4'-pentylcyclohexyl)cyclohexylcarbonyl chloride was obtained by causing a corresponding carboxylic acid to react with thionyl chloride. Next, this solution was extracted with 20 ml of dichloromethane and 150 ml of water, and the organic layer was washed with 150 ml of water, dried over MgSO$_4$, and filtered. The filtrate obtained after filtration was concentrated. Thereafter, the residue thus obtained was purified by silica gel column chromatography (developer liquid: dichloromethane), and subsequently, the residue was recrystallized from dichloromethane-methanol. Thereby, a birefringence improving agent represented by the following formula was obtained as a white solid. The amount of the compound thus obtained was 0.659 g, and the yield was 89.8%.

[Chemical Formula 18]

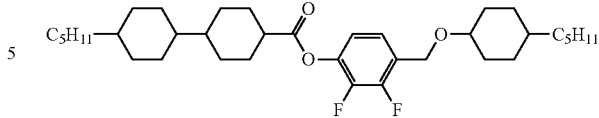

The results of $^1$H-NMR for the birefringence improving agent represented by the above formula thus obtained were as follows:

$^1$H-NMR (400 MHz, CDCl$_3$, TMS): δ (ppm) 0.83-1.32 (m, 36H, CH+CH$_2$+CH$_3$), 1.50-1.59 (m, 2H, CH$_2$), 1.70-1.87 (m, 8H, CH$_2$), 2.05-2.08 (m, 2H, CH$_2$), 2.15-2.18 (m, 2H, CH$_2$), 2.47-2.545 (m, 1H, CHCO), 3.25-3.325 (m, 1H, OCH), 4.59 (s, 2H, ArCH$_2$O), 6.845-6.89 (in, 1H, arom. H), 7.16-7.205 (m, 1H, arom. H), and furthermore, the analysis result of MALDI-TOF-MS (matrix: dithranol+TFANa) was m/z=598.83 ([M+Na]$^+$)

Examples 3 to 12 and Comparative Example 1

(Ferroelectric Liquid Crystal Composition)

Ferroelectric liquid crystal compositions were prepared using compounds A to G shown below, as indicated in the following Table 3. Incidentally, the content of the host liquid crystals IV-1 to IV-4 was respectively of equal ratios.

[Chemical Formula 19]

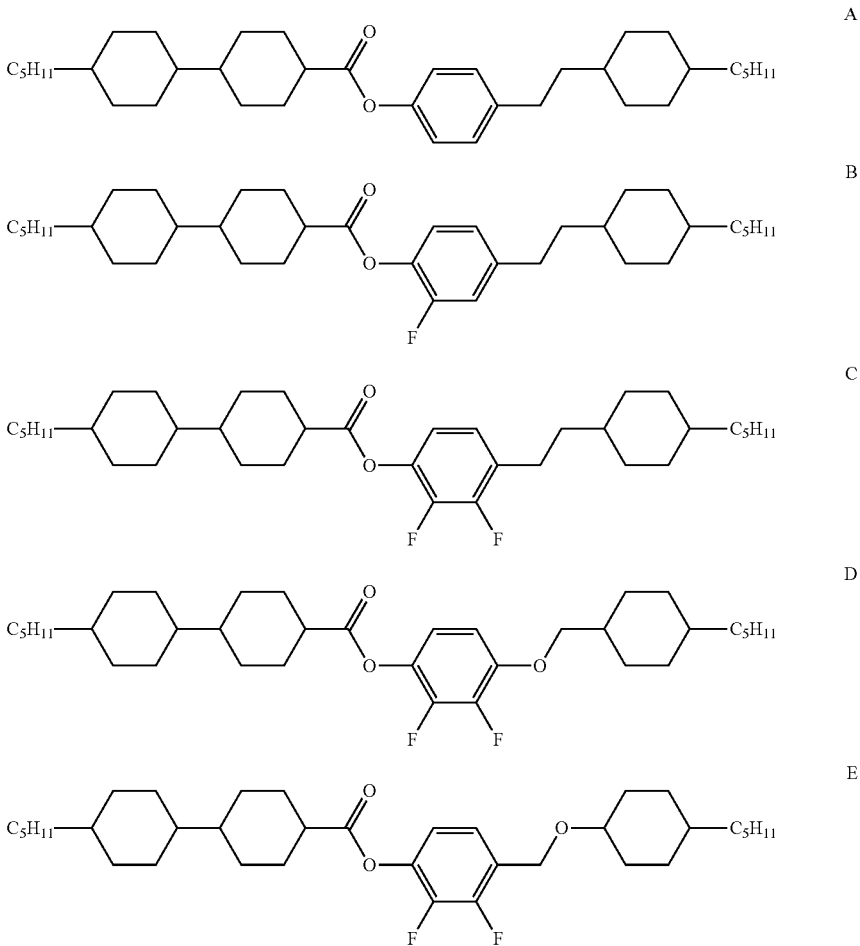

-continued

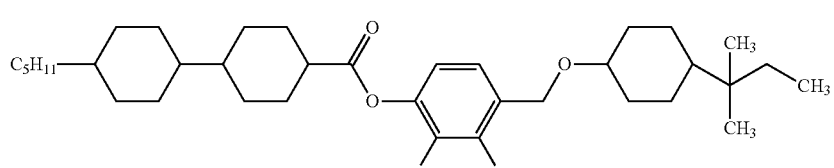
F

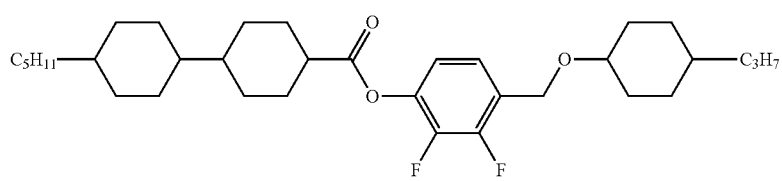
G

TABLE 3

|  | | Content (mass %) | | | | | | | | | |
|---|---|---|---|---|---|---|---|---|---|---|---|
|  | | Com. Ex. | Example | | | | | | | | |
| Ferroelectric Liquid Crystal Composition | | 1 | 3 | 4 | 5 | 6 | 7 | 8 | 9 | 10 | 11 | 12 |
| Host Liquid Crystal | I. (F,F-substituted benzoate with C8H17O and OC8H17) | | | | | | 10 | | | | | |
|  | II. (pyrimidine with C8H17O and difluorophenyl-OC10H21) | | | | | | | 10 | | | | |
|  | III. (C10H21-pyrimidine-phenyl-ester-cyclohexyl-C5H11) | | | | | | | | 10 | | | |
| | IV-1. 2-(4-Octyloxy-phenyl)-5-decylpyrimidine<br>IV-2. 2-(4-Dodecyloxy-phenyl)-5-octylpyrimidine<br>IV-3. 2-(4-Decyloxy-phenyl)-5-octylpyrimidine<br>IV-4. 5-Heptyl-2-(4'-octyl-biphenyl-4-yl)-pyrimidine | 50 | 40 | 45 | 40 | 30 | 20 | | | 40 | | |
| Chiral Compound | (C8H17-biphenyl-methylphenyl-phenyl-O-CH(CH3)-C(O)-O-C2H5) | | | | | | | | 20 | | | |
| Double Refraction Improving Agent | Not added, or any one of A to G | 0 | A: 10 | B: 5 | B: 10 | B: 20 | B: 30 | C: 10 | D: 10 | E: 10 | F: 10 | G: 10 |

(Production of Liquid Crystal Display Device)

First, on an ITO-coated glass substrate 1, a resin spacer having a circular shape with a diameter of 5.0 μm and a height of 2.7 am was formed at a pitch of 0.1 mm. Next, a rubbing alignment layer material (SE610™: Nissan Chemical Industries, Ltd.) was spin-coated thereon for 30 seconds at a speed of rotation of 1500 rpm. Thereafter, the assembly was dried in an oven at 180° C. for 30 minutes, and then a rubbing treatment was carried out.

Furthermore, on an ITO-coated glass substrate 2, a solution of a photo-isomerization type photo alignment layer material (LIA012™: DIC Corp.) was spin-coated for 30 seconds at 1500 rpm. Thereafter, the assembly was dried in an oven at 100° C. for 3 minutes, and then the assembly was subjected to a polarization exposure treatment at 2 J with a polarization exposure machine.

Next, a sealing material was applied in the form of a rectangular rim on the substrate. On that substrate, the ferroelectric liquid crystal composition described above was applied in the form of dots, and the two substrates were assembled such that the direction of the rubbing treatment and the direction of polarization treatment would be perpendicular to each other. The assembly was subjected to hot pressing. Thereafter, the liquid crystal cell was cooled, and the ferroelectric liquid crystal composition was aligned. The thickness of the liquid crystal layer was 2.7 μm.

(Evaluation)

1. Chromaticity

The birefringence of the liquid crystal display device was evaluated by installing a microspectroscopic system TFCAM-7000™ by Lambda Vision Inc. on a polarizing microscope BX51™ by Olympus Corp., and measuring chromaticity. First, two sheets of polarizing plates in the polarizing microscope were set up in a parallel state, and the chromaticity of a blank cell which was not filled with a ferroelectric liquid crystal composition was measured. The standard light source was measured. Thereafter, the two sheets of polarizing plates in the polarizing microscope were set up in a crossed Nicol state, and a liquid crystal cell filled with a ferroelectric liquid composition was rotated up to a position at which the amount of light transmission reaches the maximum. While maintaining the state, chromaticity was measured.

2. Luminance

The luminance of the liquid crystal display device was measured simultaneously with the chromaticity described above. Therefore, the specific measurement method is the same as the method for measuring the chromaticity described above.

3. Tilt Angle

The angle by which liquid crystal molecules moved was measured with a polarizing microscope. A liquid crystal cell filled with a ferroelectric liquid crystal composition was placed between two sheets of polarizing plates that were set up in a crossed Nicol state. The position of a black display in a state without voltage application was designated as the reference, and the angle by which the liquid crystal molecules that moved when a positive voltage (10 V) and a negative voltage (-10 V) were applied, was measured.

4. Transmittance

The transmittance of the liquid crystal display device was calculated from the tilt angle.

Here, the transmittance I of a liquid crystal display device can be generally determined by the following formula (a):

$$I = I_0 \sin^2(2\theta) \times \sin^2(\Delta nd/\lambda) \qquad (a)$$

wherein in the formula (a), $I_0$: intensity of incident light (constant), $\theta$: tilt angle, $\Delta n$: birefringence, d: cell gap, $\lambda$: wavelength.

In the present Example, the term of $\sin^2(2\theta)$ in the formula (a) was calculated respectively from the tilt angle $\theta_1$ at the time of application of a positive voltage, and the tilt angle $\theta_2$ at the time of application of a negative voltage, and the average thereof was designated as transmittance T.

$$T = \{\sin^2(2\theta_1) + \sin^2(2\theta_2)\}/2 \qquad (b)$$

Incidentally, in the formula (a), if the term of $\sin^2(2\theta)$ increases, transmittance I also increases. Therefore, if transmittance T is high, it can be said that the transmittance of the liquid crystal display device is high.

The evaluation results are presented in Table 4. Also, a chromaticity diagram is presented in FIG. 3.

TABLE 4

| | Birefringence Improving Agent | Chromaticity | | Luminance | Tilt Angle (degree) (60 Hz, square waves) | | | Transmittance (±10 V) |
|---|---|---|---|---|---|---|---|---|
| | | x | y | Y | Positive Voltage | Negative Voltage | Total | (%) |
| Com. Ex. 1 | — | 0.4149 | 0.3569 | 591.0737 | 42.5 | 23 | 65.5 | 75.5 |
| Example 3 | A | 0.4342 | 0.4023 | 661.2237 | 40.5 | 21 | 61.5 | 71.2 |
| Example 4 | B | 0.4312 | 0.3743 | 585.4074 | 43 | 22 | 65 | 73.9 |
| Example 5 | B | 0.4465 | 0.4009 | 621.7475 | 42 | 22.5 | 64.5 | 74.5 |
| Example 6 | B | 0.4663 | 0.452 | 757.893 | 42 | 22.5 | 64.5 | 74.5 |
| Example 7 | B | 0.4631 | 0.4795 | 875.8574 | 42 | 22.5 | 64.5 | 74.5 |
| Example 8 | C | 0.4426 | 0.4073 | 681.7248 | 41.5 | 21.5 | 63 | 72.5 |
| Example 9 | D | 0.439 | 0.4122 | 718.3195 | 43 | 22.5 | 65.5 | 74.8 |
| Example 10 | E | 0.4307 | 0.4018 | 688.2387 | 42.5 | 22 | 64.5 | 73.7 |
| Example 11 | F | 0.432 | 0.3995 | 704.538 | 40 | 22 | 62 | 72.6 |
| Example 12 | G | 0.4385 | 0.3915 | 639.1367 | 42 | 22.5 | 64.5 | 74.5 |

Figure 3:
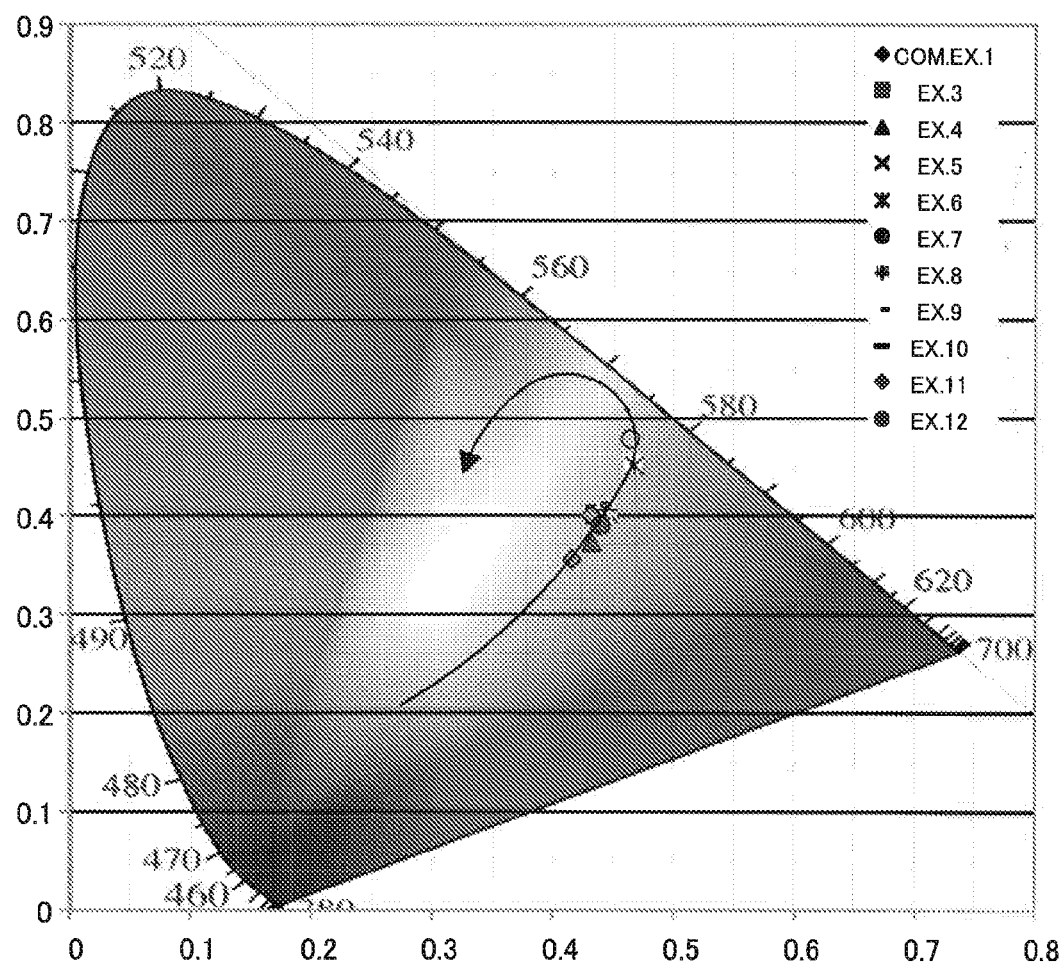
FIG. 3 is a chromaticity diagram of the liquid crystal display devices of Examples.

In regard to the chromaticity diagram shown in FIG. 3, it can be said that birefringence decreases in the direction of the arrow, and the color becomes closer to white color. That is, liquid crystal display devices that use the ferroelectric liquid crystal compositions of Example 3 to Example 12 to which the compounds A to G represented by general formula (1) or (2) of the present invention reduce birefringence as compared with the liquid crystal display device of Comparative Example 1 to which the compounds A to G were not added, and the color became closer to white color. Furthermore, the liquid crystal display devices of Example 3 to Example 12 exhibited luminance values that were higher than or equal to the luminance of the liquid crystal display device of Comparative Example 1, and a satisfactory white display could be realized. Furthermore, in the liquid crystal display devices of Example 3 to Example 12, the tilt angle becoming extremely small could be suppressed, and transmittance values equivalent to the transmittance of the liquid crystal display device of Comparative Example 1 could be obtained.

Furthermore, in the liquid crystal display devices of Example 4 to Example 12 to which the compounds B to G having the benzene ring substituted with at least F were added, the tilt angle of the liquid crystal molecules could be made larger as compared with the liquid crystal display device of Example 3 to which the compound A that did not have the benzene ring substituted with F was added, and the transmittance of the liquid crystal display devices could be increased.

REFERENCE SIGNS LIST 1 liquid crystal display device
2a first base material 2b second base material
3a first electrode layer
3b second electrode layer
4a first alignment layer
4b second alignment layer
5 liquid crystal layer
11a first alignment treatment substrate
11b second alignment treatment substrate

The invention claimed is:
1. A compound of formula:

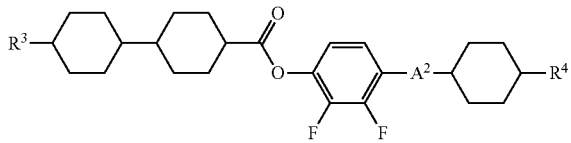

wherein:
R³ and R⁴ are linear or branched alkyl groups having 3 to 9 carbon atoms, provided that at least one of R¹ and R⁴ has 5 or more carbon atoms; and
A² is —O—CH₂— or —CH₂—O—.

2. The compound of claim 1, wherein both of R¹ and R² are alkyl groups having 5 carbon atoms.

3. The compound of claim 1, wherein at least one of R³ or R⁴ is an alkyl group having 5 carbon atoms.

4. The compound of claim 1, wherein both of R¹ and R² are alkyl groups having 5 carbon atoms.

5. A ferroelectric liquid crystal composition comprising one or more birefringence improving agents of claim 1.

6. The ferroelectric liquid crystal composition of claim 5, further comprising one or more birefringence improving agents of formula:

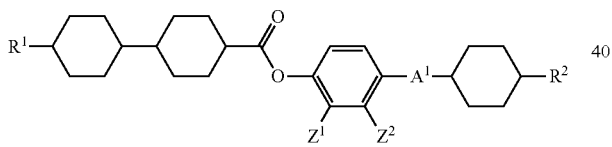

wherein:
R¹ and R² are linear or branched alkyl groups having 3 to 9 carbon atoms, provided that at least one of R¹ and R² has 5 or more carbon atoms;
A¹ is —CH₂—CH₂—, —O—CH₂— or —CH₂—O—; and
Z¹ and Z² are each independently a fluorine atom or a hydrogen atom.

7. The ferroelectric liquid crystal composition of claim 5, further comprising a chiral compound A, a chiral compound B or a mixture thereof, wherein chiral compound A is of formula:

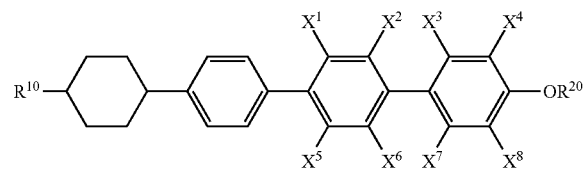

and
chiral compound B is of formula:

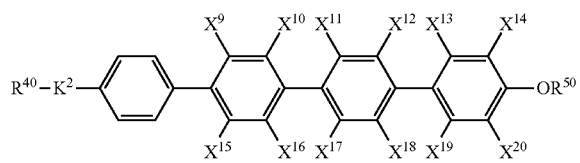

wherein:
X¹ to X⁸ and X⁹ to X²⁰, each independently is —CH₃, —CF₃, a halogen atom, or a hydrogen atom;
K² is a single bond or a cyclohexane ring;
R¹⁰ and R⁴⁰ are non-chiral groups which are saturated or unsaturated, linear or branched alkyl or alkoxyalkyl groups, which groups are optionally substituted with a halogen atom; and
R²⁰ and R⁵⁰ are chiral groups of formula:

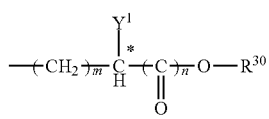

wherein:
R³⁰ is a saturated or unsaturated linear, branched or cyclic alkyl group or alkoxyalkyl group having 1 to 10 carbon atoms, which groups are optionally substituted with a halogen atom;
Y¹ is —CH₃ or a fluorine atom;
m is 0 or 1,
n is 0 or 1, and
the symbol * indicates the chiral center.

8. The ferroelectric liquid crystal composition of claim 7, further comprising the compound A, but not the compound B.

9. The ferroelectric liquid crystal composition of claim 7, further comprising the compound B, but not the compound A.

10. The ferroelectric liquid crystal composition of claim 7, further comprising a mixture of the compound B, and the compound A.

11. A liquid crystal display device comprising:
a first alignment treatment substrate comprising a first base material, a first electrode layer formed on the first base material, and a first alignment layer formed on the first electrode layer;
a second alignment treatment substrate comprising a second base material, a second electrode layer formed on the second base material, and a second alignment layer formed on the second electrode, layer; and
a liquid crystal layer that is formed between the first alignment layer and the second alignment layer and which contains a ferroelectric liquid crystal composition,
wherein the ferroelectric liquid crystal composition contains a birefringence improving agent of formula:

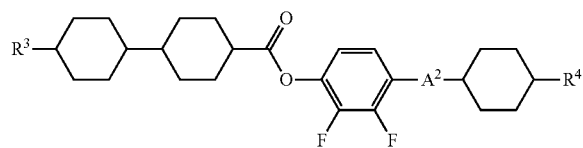

wherein:
R³ and R⁴ are linear or branched alkyl groups having 3 to 9 carbon atoms, provided that at least one of R¹ and R⁴ has 5 or more carbon atoms; and
A² is —O—CH₂— or —CH₂—O—.

12. The liquid crystal display device of claim 11, wherein the ferroelectric liquid crystal composition contains from 5% to 60% by mass of the birefringence improving agent.

13. The liquid crystal display device of claim 11, wherein the ferroelectric liquid crystal composition further comprises a chiral compound A, a chiral compound B or a mixture thereof, wherein chiral compound A is of formula:

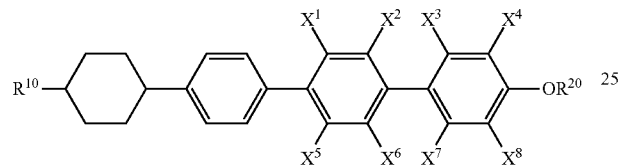

and
chiral compound B is of formula:

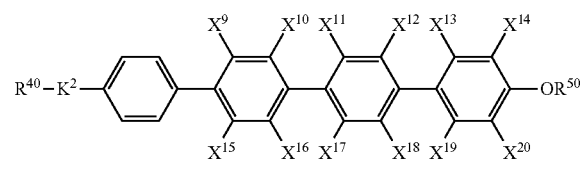

wherein:
$X^1$ to $X^8$ and $X^9$ to $X^{20}$, each independently is —CH₃, —CF₃, a halogen atom, or a hydrogen atom;
$K^2$ is a single bond or a cyclohexane ring;
$R^{10}$ and $R^{40}$ are non-chiral groups which are saturated or unsaturated, linear or branched alkyl or alkoxyalkyl groups, which groups are optionally substituted with a halogen atom; and
$R^{20}$ and $R^{50}$ are chiral groups of formula:

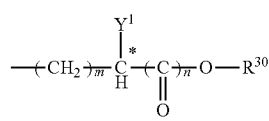

wherein:
$R^{30}$ is a saturated or unsaturated linear, branched or cyclic alkyl group or alkoxyalkyl group having 1 to 10 carbon atoms, which groups are optionally substituted with a halogen atom;
$Y^1$ is —CH₃ or a fluorine atom;
m is 0 or 1,
n is 0 or 1, and
the symbol * indicates the chiral center.

14. The liquid crystal display device of claim 13, wherein the ferroelectric liquid crystal composition further comprises the compound A, but not the compound B.

15. The liquid crystal display device of claim 13, wherein the ferroelectric liquid crystal composition further comprises the compound B, but not the compound A.

16. The liquid crystal display device of claim 13, wherein the ferroelectric liquid crystal composition further comprises a mixture of the compound B, and the compound A.

* * * * *